US007550431B2

(12) United States Patent
Deslongchamps et al.

(10) Patent No.: US 7,550,431 B2
(45) Date of Patent: Jun. 23, 2009

(54) SPATIALLY-DEFINED MACROCYCLES INCORPORATING PEPTIDE BOND SURROGATES

(75) Inventors: Pierre Deslongchamps, Québec (CA); Yves Dory, Québec (CA); Luc Ouellet, Québec (CA); Gérald Villeneuve, Québec (CA); Mahesh Ramaseshan, Sunnyvale, CA (US); Daniel Fortin, Québec (CA); Mark L. Peterson, Québec (CA); Hamid R. Hoveyda, Brussels (BE); Sylvie Beaubien, Québec (CA); Éric Marsault, Québec (CA); Graeme L. Fraser, Rixensart (BE)

(73) Assignee: Tranzyme Pharma Inc., Quebec (CA)

(*) Notice: Subject to any disclaimer, the term of this patent is extended or adjusted under 35 U.S.C. 154(b) by 74 days.

(21) Appl. No.: 10/911,219

(22) Filed: Aug. 2, 2004

(65) Prior Publication Data

US 2005/0119169 A1 Jun. 2, 2005

Related U.S. Application Data

(60) Provisional application No. 60/491,250, filed on Jul. 31, 2003, provisional application No. 60/491,253, filed on Jul. 31, 2003, provisional application No. 60/491,249, filed on Jul. 31, 2003.

(51) Int. Cl.
*A61K 38/12* (2006.01)
*C07K 5/12* (2006.01)
(52) U.S. Cl. .......................... 514/11; 530/317
(58) Field of Classification Search ............... None
See application file for complete search history.

(56) References Cited

U.S. PATENT DOCUMENTS

| 5,770,687 | A | 6/1998 | Hornik et al. |
| 5,874,529 | A | 2/1999 | Gilon et al. |
| 6,051,554 | A | 4/2000 | Hornik et al. |
| 6,165,985 | A | 12/2000 | Jasserand et al. |
| 2005/0054562 | A1* | 3/2005 | Fraser et al. ............ 514/9 |
| 2006/0025566 | A1* | 2/2006 | Hoveyda et al. ......... 530/317 |

FOREIGN PATENT DOCUMENTS

| EP | 1 312 612 A1 | 5/2003 |
| WO | WO-98/04583 A1 | 2/1998 |
| WO | WO-98/54577 A1 | 12/1998 |
| WO | WO-99/65508 A1 | 12/1999 |
| WO | WO-01/25257 A2 | 4/2001 |
| WO | WO-02/062819 A2 | 8/2002 |

OTHER PUBLICATIONS

M.A. Dechantsreiter, et al. J. Med. Chem. (1999) 42, 3033-3040.*
M. Sukopp, et al. Helv. Chim. Acta. (2002) 85, pp. 4442-4452.*
Adessi, Celine, et al., "Converting a Peptide into a Drug: Strategies to Improve Stability and Bioavailability", Current Medicinal Chemistry, 2002, vol. 9, pp. 963-978.
Glenn, Matthew P. et al., "Mimetics of the Peptide β-Strand", Mini Reviews in Medicinal Chemistry, 2002, vol. 2, pp. 433-445.
Steer, David L., et al., "β-Amino Acids: Versatile Peptidomimetics", Current Medicinal Chemistry, 2002, vol. 9, pp. 811-822.
EPO Supplementary Partial European Search Report for EP 04 761 607.3, Jul. 25, 2006.
Haramura, M, et al., Design and synthesis of N-terminal cyclic motilin partial peptides: a novel pure motilin antagonist, Chemical and Pharmaceutical Bulletin (Jan. 2001), pp. 40-43, 49:1.
Inge Depoortere, et al., Interaction of the growth hormone-releasing peptides ghrelin and growth-hormone releasing peptide-6 with motilin receptor in the rabbit gastric antrum, The Journal of Pharmacology and Experimental Therapeutics (2003), pp. 660-666, 305:2.
Khiat, A, et al., Identification of the motilide pharmacophores using quantitative structure activity relationships, Journal of Peptide Research (Oct. 1, 1998), pp. 321-328, 52:4.
Koga, H, et al., Macrolide-type motilin receptor agonists: assessment of the biological value of the 2'- and 4"-hydroxyl groups of acid-stable 8,9-anhydroerythromycin A 6,9- hemiacetals, Bioorganic & Medicinal Chemistry Letters (1994), pp. 1649-1654, 4:13.
Haramura, M, et al., Design and synthesis of motilin antagonists derived from the [1-4] fragment of porcine motilin, Journal of Medicinal Chemistry (Jan. 31, 2002), pp. 670-675, 45:3.
Takanashi, H, et al., Selective motilin receptor antagonist in the smooth muscle of the rabbit small intestine, Journal of Pharmacology and Experimental Therapeutics (1995), pp. 624-628, 273:2.
Horton, Douglas A., et al., "Exploring privileged structures: The combinatorial synthesis of cyclic peprides", Molecular Diversity, 2002, vol. 5, pp. 289-304.
Tyndall, Joel D.A., et al., "Macrocycles Mimic the Extended Peptide Conformation Recognized By Aspartic, Serine, Cysteine and Metallo Proteases", Current Medicinal Chemistry, 2001, vol. 8, 99. 893-907.
Boer, Jurgen, et al., "Design and Synthesis of Potent and Selective a4b7 Integrin Antagonists", J. Med. Chem., 2001, vol. 44, pp. 2586-2595.
Kramer, Oliver H., et al., "Histone deacetylase as a therapeutic target", Trends in Endocrinology & Metabolism, vol. 12, No. 7, Sep. 2001, pp. 294-300.

(Continued)

*Primary Examiner*—Andrew D Kosar
(74) *Attorney, Agent, or Firm*—Myers Bigel Sibley & Sajovec, PA

(57) ABSTRACT

Novel spatially-defined macrocyclic compounds incorporating peptide bond surrogates are disclosed. Libraries of these macrocycles are then used to select one or more macrocycle species that exhibit a specific interaction with a particular biological target. In particular, compounds according to the invention are disclosed as agonists or antagonists of a mammalian motilin receptor and a mammalian ghrelin receptor.

3 Claims, 7 Drawing Sheets

OTHER PUBLICATIONS

Meinke, Peter T., et al., "Histone Deacetylase: A Target for Antiproliferative and Antiprotozoal Agents", Current Medicinal Chemistry, 2001, vol. 8, pp. 211-235.

Kinney, William A., et al., "Structure-Function Analysis of Urotensin II and Its Use in the Construction of a Ligand-Receptor Working Model", Angew. Chem. Int. Ed., 2002, vol. 41, No. 16, pp. 2940-2944.

Giolitti, Alessandro, et al., "Monocyclic Human Tachykinin NK-2 Receptor Antagonists as Evolution of a Potent Bicyclic Antagonist: QSAR and Site-Directed Mutagenesis Studies", J. Med. Chem., 2002, vol. 45, pp. 3418-3429.

Maliartchouk, Sergei, et al., "A Designed Peptidomimetic Agonistic Ligand of TrkA Nerve Growth Factor Receptors", Molecular Pharmacology, vol. 57, pp. 385-391.

Lee, Hong Boon, et al., "Syntheses and Activities of New C10 B-Turn Peptidomimetics", J. Org. Chem., 2004, vol. 69, pp. 701-713.

Jefferson, Elizabeth A., et al., "New Inhibitors of Bacterial Protein Synthesis from a Combinatorial Library of Macrocyles", J. Med. Chem., 2002, vol. 45; pp. 3430-3439.

Paczkowski, Natalii J., et al., "Pharmacological characterization of antagonists of the C5a receptor", British Journal of Pharmacology, 1999, vol. 128, pp. 1461-1466.

Kirshenbaum, Kent, et al., "Designing polymers that mimic biomolecules", Current Opinion in Structural Biology, 1999, vol. 9, pp. 530-535.

Hill, David J., et al., "A Field Guide to Foldamers", Chem. Rev., 2001, vol. 101, pp. 3893-4011.

Patch, James A., et al., "Mimicry of bioactive peptides via non-natural, sequence-specific peptidomimetric obligomers", Current Opinion in Chemical Biology, 2002, vol. 6, pp. 872-877.

Ripka, Amy S., et al., "Peptidomimetric design", Current Opinion in Chemical Biology, 1998, vol. 2, pp. 441-452.

Gante, Joachim, "Peptidomimetics—Tailored Enyzme Inhibitors", Angew. Chem. Int. Ed. Engl., 1994, vol. 33, pp. 1699-1720.

Olson, Gary L., et al., "Concepts and Progress in the Development of Peptide Mimetics", Journal of Medicinal Chemistry, Oct. 15, 1993, vol. 36, No. 21, pp. 3039-3049.

Shin, Injae, et al., "Synthesis of Optically Active Phthaloyl D-Aminooxy Acids from L-Amino Acids or L-Hydroxy Acids as Building Blocks for the Preparation of Aminooxy Peptides", J. Org. Chem., 2000, vol. 65, pp. 7667-7675.

Gilon, Chaim, et al., "Backbone Civiization: A New Method for Conferring Conformational Constraint on Peptides", The Hebrew University of Jerusalem, 1990, pp. 745-750.

Palucki, Brenda L., et al., "Spiro(indoline-3,4'-piperidine) Growth Hormone Secretagogues as Ghrelin Mimetics", Bioorganic & Medicinal Chemistry Letters, 2001, vol. 11, pp. 1955-1957.

Bednarek, Maria A., et al., "Structure-Function Studies on the New Growth Hormone-Releasing Peptide, Ghrelin: Minimal Sequence of Ghrelin Necessary for Activation of Growth Hormone Secretagogue Receptor 1a", J. Med. Chem., 2000, vol. 43, pp. 4370-4376.

Shemyakin, M.M., "Chemistry of Depsipeptide Antibiotics", Antimicrobial Agents and Chemotherapy—1965, pp. 962-976.

Moore, R.E., "Cyclic peptides and depsipeptides from cyanobacteria: a review", Journal of Industrial Microbiology (1996), vol. 16, pp. 134-143.

Ballard, C.E., "Recent Developments in Depsipeptide Research", Current Medicinal Chemistry 2002, vol. 9, pp. 471-498.

Ahn, Jung-Mo, et al., "Peptidomimetics and Peptide Backbone Modifications", Mini Reviews in Medicinal Chemistry, 2002, vol. 2, pp. 463-473.

Eguchi, Masakatsu, et al., "Design, Synthesis, and Application of Peptide Secondary Structure Mimetics", Mini Reviews in Medicinal Chemistry, 2002, vol. 2, pp. 447-462.

Venkatesan, Natarajan, et al., "Synthesis and Enzyme Inhibitory Activities of Novel Peptide Isosteres", Current Medicinal Chemistry, 2002, vol. 9, pp. 2243-2270.

Perez, Juan J., et al., "Molecular Modeling in the Design of Peptidomimetics and Peptide Surrogates", Current Medicinal Chemistry, 2002, vol. 9, pp. 2209-2229.

\* cited by examiner

Reagents and conditions: a) K₂CO₃, PhSH, DMF; b) n-Pr-NH₂, mercaptoethanol, DMF; c) BtsGlyOH, DIC, DCM; d) BtsGlyOH, DEBPT, DIPEA, DMF

SPATIALLY-DEFINED MACROCYCLES INCORPORATING PEPTIDE BOND SURROGATES

FIELD OF THE INVENTION

This invention relates to spatially-defined macrocyclic compounds incorporating peptide bond surrogates. It also relates to the generation of libraries of these macrocycles. These libraries are then used to select one or more macrocycle species that exhibit a specific interaction with a particular biological target.

BACKGROUND OF THE INVENTION

Peptides have been at the forefront of combinatorial chemistry technology development due to their ease of synthesis on solid support, the reproducible and high-yielding reactions involved, and the ready availability of starting materials. Peptides are the endogenous ligands for a number of enzymes and receptors. Modifications of these peptides can be performed to develop even more potent agonists or inhibitors of these same receptors and enzymes. In addition, combinatorial peptide libraries have been used to find a number of previously unknown active sequences for a wide array of enzyme and receptor systems. However, these novel materials are still plagued by the usual limitations associated with the direct use of peptides as pharmaceuticals, although many are used in human and veterinary medicine due to their potency and selectivity. Although peptides are highly potent and selective biological agents, their use as pharmaceutical products is limited by Poor aqueous solubility
Metabolic instability, particularly to proteases
Low oral bioavailability
Inadequate membrane permeability
Difficulty in transport to site of action in tissues and organs
Potential antigenicity
Short pharmacokinetic half-life decreases duration of pharmacological action
Side effects due to the presence of receptors for the peptide in other non-target areas of an organism
High manufacturing costs In order to circumvent these drawbacks while retaining the high potency of the peptide, significant work over the past three decades has been devoted to the study of mimics of these peptides, or peptidomimetics. Replacement of one or more amide bonds with functional groups that have similar structural characteristics, but different metabolic profiles has been pursued widely. Similarly, restriction of conformation of the resulting molecules utilizing either sterically demanding or structurally restricted amino acids to specifically display side chains in space. Cyclization of the linear peptide is also traditionally pursued.

However, the ability to control conformation within a single cyclic molecule often requires long experimentation in order to access the desired structure. Of greater interest would be the ability to direct and control the three-dimensional orientation so as to probe multiple conformations with the same interacting peptide side chain functionalities. In this manner, the optimal one for the biological target of interest could be rapidly determined.

Recently, WO 01/25257 has described the use of specific elements termed "tethers" to control the conformations within macrocyclic peptidomimetics. However, to date, no method has been described to combine the use of such tether elements with peptide bond surrogates.

Such molecules would have unique and superior properties over other analogues:
Ease of synthesis
Enhanced chemical stability
Improved metabolic stability
Better selectivity with lower incidence of side effects
More favorable pharmacokinetics
Better oral bioavailability
Higher aqueous solubility In particular, these analogues possess advantages that make them desirable as pharmaceutical agents with improved therapeutic properties:
Additional interacting functionalities
Modulated physicochemical properties
Modified conformations to those of cyclic peptides that are dictated primarily by the amide bond The use of backbone to backbone cyclization to control conformation of peptidic molecules has been described. (Gilon, G. *Biopolymers* 1991, 31, 745). However, this approach provides a constraint with the only control being provided by the length of the backbone chain employed. This does not permit access to all the conformations that might be require in order to optimally interact within a biological system. Nonetheless, this approach has yielded somatostatin analogues that can be used for therapeutic (WO 98/04583, WO 99/65508, U.S. Pat. No. 5,770,687, U.S. Pat. No. 6,051,554) or diagnostic purposes (WO 02/062819), bradykinin analogues (U.S. Pat. No. 5,874,529).

On the other hand, cyclic peptides offer a number of benefits compared with the corresponding linear analogues, including restricted conformational mobility, defined topology, enhanced stability to proteolytic enzymes and modified polarity (*Molecular Diversity* 2000 (pub. 2002), 5,289-304).

Accordingly, cyclic structures can greatly improve the pharmacological and pharmacokinetic profiles of peptides. Examples demonstrate that cyclic peptides can enhance potency, selectivity, stability, bioavailability and membrane permeability. The stability to enzymatic degradation of the cyclic structure arises from the difficulty of such molecules to attain the extended conformation required to be recognized as a substrate for peptidases. Very large mixture libraries ($10^8$ members or more) of cyclic peptides have been described in WO 98/54577.

Until recently, the number of reports of the use of macrocyclic peptidomimetics in drug discovery has rather been limited. Recent examples of therapeutically interesting bioactivities that have been displayed by small peptide or peptidomimetic macrocycles include protease inhibition (HIV, cancer, inflammation)—*Curr. Med. Chem.* 2001, 8, 893-907; Integrin receptor antagonists (cell adhesion inhibition, inflammation, diabetes)—*J. Med. Chem.* 2001, 44, 2586-2592; Histone deacetylase inhibition (cancer, anti-fungal)—*Tr. Endocrin. Metabol.* 2001, 12, 294-300; *Curr. Med. Chem.* 2001, 8, 211-235; Urotensin II antagonists (cardiovascular disease)—*Angew. Chem. Int. Ed.* 2002, 41, 2940-2944; neurokinin-2 antagonists (asthma, irritable bowel syndrome)—*J. Med. Chem.* 2002, 45, 3418-3429; tyrosine receptor kinase A (TrkA) antagonists and neurotrophin-3 mimetics (Alzheimer's, stroke, diabetic neuropathy)—*Mol. Pharm.* 2000, 57, 385-391; *J. Org. Chem.* 2004; 69, 701-713; antibacterial agents—*J. Med. Chem.* 2002, 45, 3430-3439; and C5a complement inhibitors (inflammatory diseases)—*Br. J. Pharmacol.* 1999, 128, 1461-1466.

However, in most of these cases, the formation of the cyclic structure was simply one step in a lengthy optimization process. The use of large macrocyclic libraries for initial hit identification and drug discovery is largely unprecedented.

This is particularly striking given the extensive efforts in combinatorial chemistry, which began focused on peptides, and the subsequent explosion in the number and type of small molecule libraries that can now be accessed.

Among the possible modifications of peptide bonds, depsipeptides are known in the art. A comparative example of a given peptide and the corresponding depsipeptide is given below. Importantly, the relative arrangement of side chains on adjacent residues is not affected as it can be with other peptide bond surrogates.

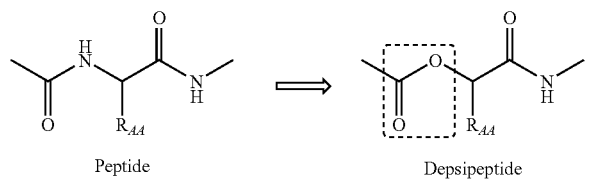

As may be noticed, one of the —NH— in the peptide is replaced by —O— in the depsipeptide.

Many depsipeptides are known to exhibit special biological activities (see Ballard, C. E.; Yu, H.; Wang, B. *Curr. Med. Chem.* 2002, 9, 471-498; Moore, R. E. *J. Ind. Microbiol.* 1996, 16, 134-143 and Shemayakin, M. M. *Antimicrob. Agents Chemother* 1965, 5, 962-976). For example, vancomycin, valinomycin, actinomycins, didemnins, dolstatins are natural product depsipeptides. Included in the therapeutic utility of these compounds are anticancer, antibacterial, antiviral (callipeltins, quinoxapeptins), antifungal (jaspamides), anti-inflammatory (neurokinin antagonists), anti-clotting, antiantherogenic (micropeptins), and other activities.

Another class of amino acid mimics, peptoids, have found wide utility in the design and synthesis of peptide-related therapeutic agents and biomaterials (*Curr. Opin. Struct. Biol.* 1999, 9, 530-535). A comparison between depsipeptides and peptoids is shown below:

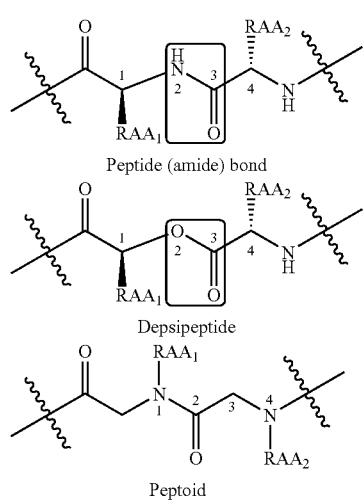

In yet another approach, the urethane moiety can function as an effective peptide bond mimic. It possesses analogous defined planarity and geometry with similar rigidity to that of an amide bond. However, this moiety is not isosteric to the amide as it contains an extra atom, so that incorporation leads to larger-sized structures. This could prove quite advantageous, however, as the unique properties of peptides containing β-amino acids attests (*Chem. Rev.* 2001, 101, 3893-4011; *Curr. Med. Chem.* 2002, 9, 811-822).

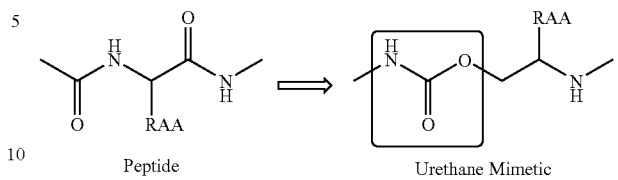

The following can be cited as potential benefits of the urethane moiety as a peptide bond surrogate:

- Modification of H-bonding properties due to the extra heteroatom for inter- and intramolecular interactions as well as in improved solubilities
- Imposition of a degree of conformational restriction
- Backbone NH and chiral R groups offer opportunities for substitution and modification for modulation of biological and physical properties
- Modified polarity, more lipophilic due to the extra carbon atom, as compared with the peptide bond
- Resistance to proteinases
- Alteration of pharmacokinetic properties Urea peptide bond surrogates have also been explored in combination with other isosteres to construct molecules with novel architecture. For example, in the development of linear tripeptidomimetics as matrix metalloproteinase inhibitors for the treatment of arthritis and cancer, ureas and sulfonamides were targeted as replacements for the amide bond. The urea substitution actually contains an N-substituent where the attached group is the same as the amino acid side chain in the original peptide and hence could be considered a urea-peptoid hybrid.

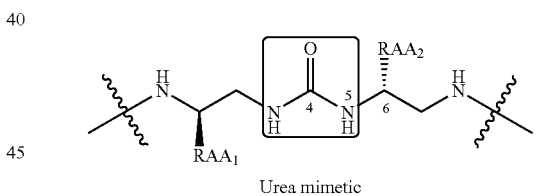

These examples highlight only a representative sampling of the variety of peptide bond surrogates that have been designed and investigated (*Mini-Rev. Med. Chem.* 2002, 2, 463-473; *Mini-Rev. Med. Chem.* 2002, 2, 447-462; *Curr. Med. Chem.* 2002, 9, 2209-2229; *Curr. Med. Chem.* 2002, 9, 2243-2270; *Curr. Med. Chem.* 2002, 9, 963-978; *Curr. Opin. Chem. Biol.* 2002, 6, 872-877; *Curr. Opin. Chem. Biol.* 1998, 2, 441-452; *Angew. Chem. Int. Ed. Engl.* 1994, 33, 1699; *J. Med. Chem.* 1993, 36, 3039-3049; *J. Org Chem.* 2000, 65, 7667-7675). Additional structures that specifically replace the peptide bond or offer an alternative type of peptide residue are shown in FIG. 3. This variety has permitted chemists to explore a number of modifications to peptide structure not accessible through natural amino acids alone. However, often this is done, not in a predictable manner, but rather determined after the construction of the molecule. Therefore, the control permitted by the aforementioned tether elements would be of utility in the context of structures containing these peptide bond surrogates.

Further, to date, peptide bond surrogates have not been widely investigated in the context of cyclic structures nor in libraries, likely due to the challenges involved in their syntheses.

Accordingly, their remains a need for macrocyclic structures incorporating a variety of peptide bond surrogates.

SUMMARY OF THE INVENTION

The present invention uses peptide bond surrogates in the context of conformationally-defined cyclic molecules. Accordingly, the invention relates to macrocyclic compounds of formula (I) which incorporate peptide bond surrogates.

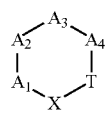
(I)

wherein $A_3$ and $A_4$ are optionally present;

$A_1$, $A_2$, $A_3$ and $A_4$ are chosen from the group consisting of formulas S1 to S21, with the proviso that at least one of $A_1$, $A_2$, $A_3$ or $A_4$ is selected from the group consisting of formulas S2 to S21

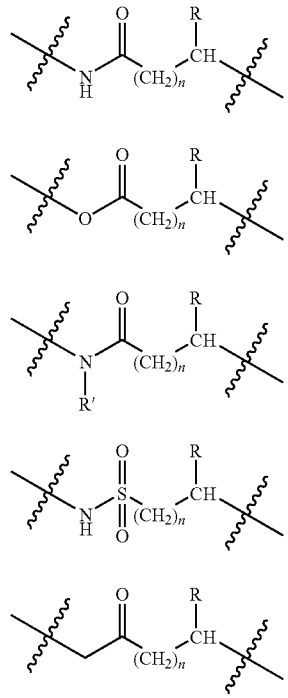

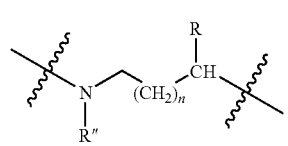

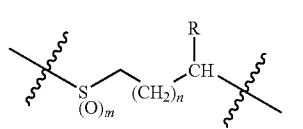
7

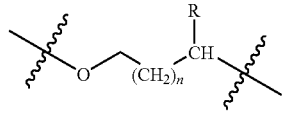
8

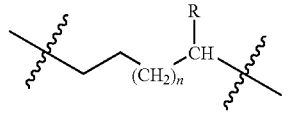
9

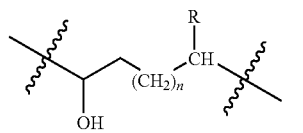
10

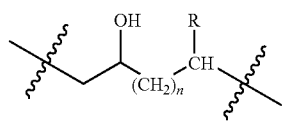
11

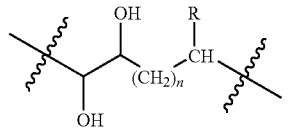
12

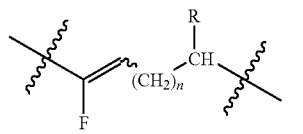
13

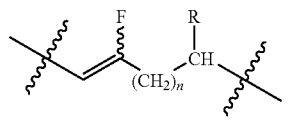
14

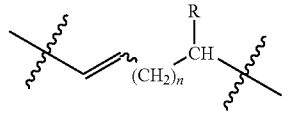
15

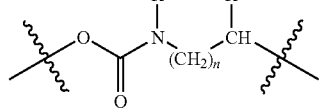
16

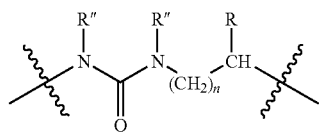
17

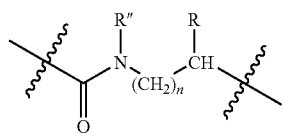
18

-continued

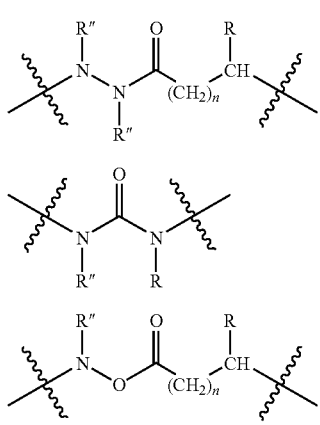

wherein R and R' are chosen from side chains of natural amino acids or side chains of unnatural amino acids, with the proviso that R' is not hydrogen;
R'' is hydrogen or alkyl;
m is 0, 1 or 2; and
n is 0, 1 or 2;
X is —O— or —$NR_1$, wherein $R_1$ is selected from the group consisting of hydrogen, alkyl, substituted alkyl, acyl and sulfonyl; and
T is a bivalent radical of formula (II):

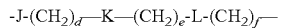  (II)

wherein:
J is bonded to X and is a bivalent radical chosen from —$CH_2$— or —C(=O)—;
d, e and f are each independently selected from 0, 1, 2, 3, 4 or 5;
L is optionally present;
K and L are independently a covalent bond or a bivalent radical selected from the group consisting of:
—O—, —$NR_2$—, —S—, —SO—, —$SO_2$—, —C(=O)—, —C(=O)—, —C(=O)—, —C(=O)—$NR_3$—, —$NR_3$—C(=O)—, —$SO_2$—$NR_4$—, —$NR_4$—$SO_2$—, —$CR_5R_6$—, —CH($OR_7$)—, —CH=CH— with a Z or E configuration, —C≡C—, and

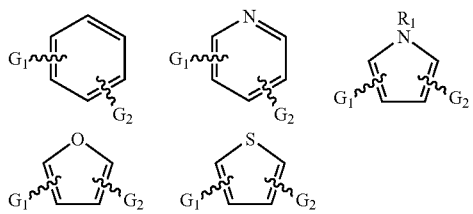

wherein $R_2$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, formyl, acyl, carboxyalkyl, carboxyaryl, amido, amidino, sulfonyl and sulfonamido;
$R_3$ and $R_4$ are independently selected from hydrogen or $C_1$-$C_6$ alkyl;
$R_5$ and $R_6$ are independently selected from the group consisting of hydrogen, alkyl, hydroxy, alkoxy, and amino, with the proviso that if one of $R_5$ or $R_6$ is hydroxy, alkoxy or amino, the other is hydrogen or alkyl;
$R_7$ is selected from the group consisting of hydrogen, alkyl, substituted alkyl, formyl and acyl; and
$G_1$ and $G_2$ are independently a covalent bond or a bivalent radical selected from the group consisting of:
—O—, —N $R_8$—, —C(=O)—, —C(=O)—, —C(=O)O—, —C(=O)$NR_9$—, —$NR_9$—C(=O)—, —$SO_2$—$NR_{10}$, —$NR_{10}$—$SO_2$—, —$CR_{11}R_{12}$—, —CH=CH— with Z or E configuration, and —C≡C—, wherein $R_8$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, formyl, acyl, carboxyalkyl, carboxyaryl, amido, amidino, sulfonyl and sulfonamido;
$R_9$ and $R_{10}$ are independently selected from hydrogen or $C_1$-$C_6$ alkyl; and
$R_{11}$ and $R_{12}$ are independently selected from the group consisting of hydrogen, alkyl, hydroxyl, alkoxy, and amino with the proviso that if one of $R_{11}$ or $R_{12}$ is hydroxyl, alkoxy or amino, the other is hydrogen or alkyl;
with the proviso that $G_1$ is the closest to J, and that $G_1$ or $G_2$ can be attached in a relative arrangement to each other of 1, 2 or 1, 3 or 1, 4.

In a second aspect of the invention, there are provided compounds of formula (III)

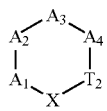 (III)

wherein $A_1$, $A_2$, $A_3$, $A_4$ and X are as defined for formula (I) and wherein $T_2$ is a bivalent radical chosen from the group consisting of:

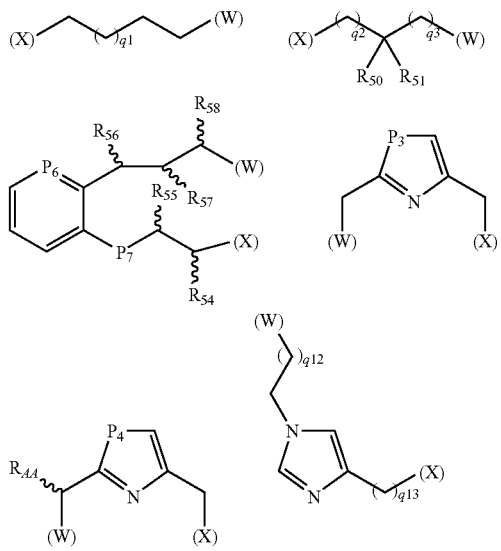

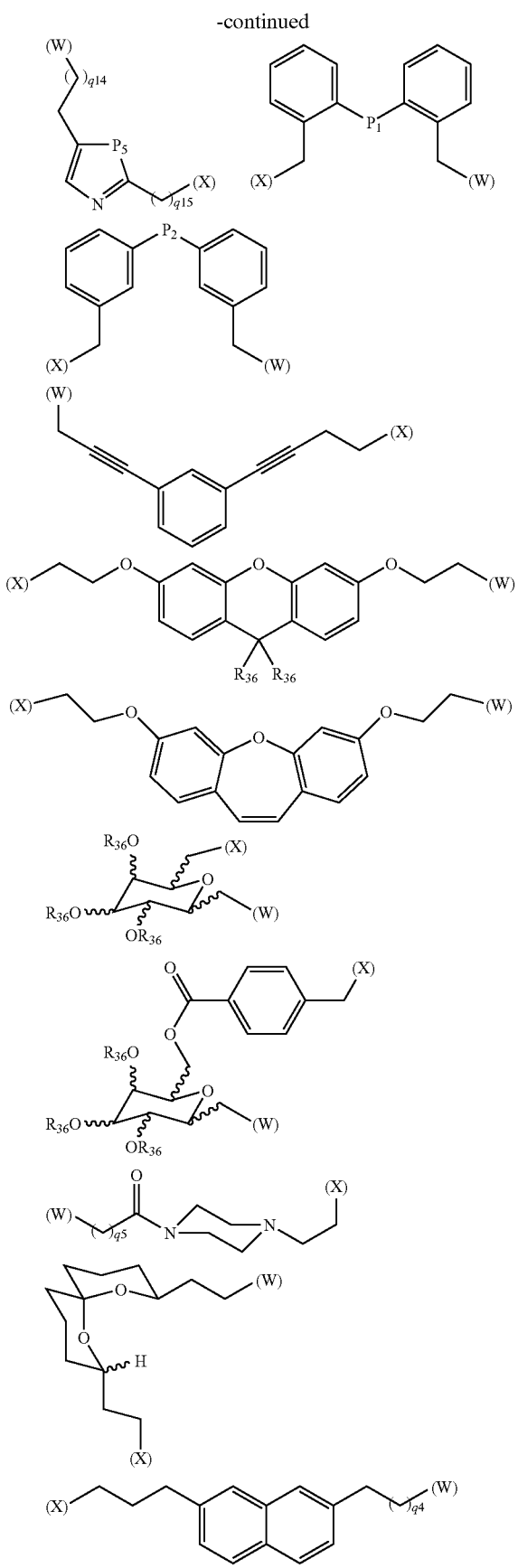
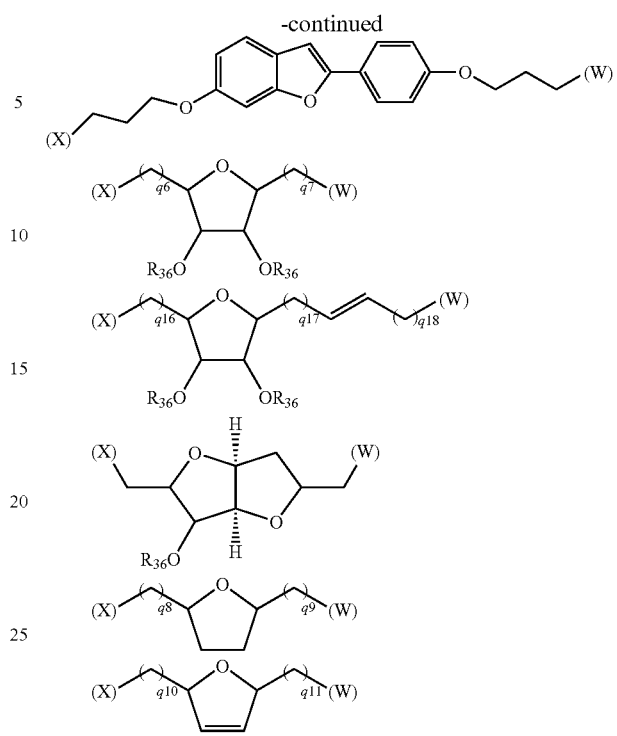

wherein the wavy lines indicate either a (R) or (S) stereochemistry or mixture thereof; $q_1$, $q_2$, $q_3$, $q_6$, $q_7$, $q_8$, $q_9$, $q_{10}$, $q_{11}$, $q_{13}$, $q_{15}$ and $q_{16}$ are each independently 1, 2, 3, 4 or 5;

$q_4$ and $q_{18}$ are independently 1 or 2;

$q_5$ is 2, 3 or 5;

$q_{12}$ and $q_{14}$ are each independently 0, 1, 2, 3 or 4;

$q_{17}$ is 0, 1, 2 or 3;

$P_1$, $P_2$, $P_3$ $P_4$ and $P_5$ are each independently O, S or NH;

$P_6$ is N or CH;

$P_7$ is O or $CR_{52}R_{53}$;

$R_{36}$ is hydrogen, $C_1$-$C_6$ alkyl, benzyl or acyl;

$R_{50}$ and $R_{51}$ are independently selected from the group consisting of hydrogen, alkyl, hydroxy, alkoxy, and amino with the proviso that if one of $R_{50}$ or $R_{51}$ is hydroxy, alkoxy or amino, the other is hydrogen or alkyl;

$R_{52}$ and $R_{53}$ are independently selected from the group consisting of hydrogen, alkyl, hydroxy, alkoxy, and amino with the proviso that if one of $R_{52}$ or $R_{53}$ is hydroxyl, alkoxy or amino, the other is hydrogen or alkyl;

$R_{54}$, $R_{55}$, $R_{56}$, $R_{57}$ and $R_{58}$ are independently selected from the group consisting of hydrogen, alkyl, hydroxy, alkoxy, and amino;

$R_{AA}$ is the side chain of a natural amino acid;

(X) indicates the point of attachment of $T_2$ to X; and (W) indicates the point of attachment of $T_2$ to $A_2$, $A_3$ or $A_4$.

The invention also provides combinatorial libraries of these macrocycles. Compounds of formula (I) and formula (III) are also disclosed as agonists or antagonists of a mammalian motilin receptor and a mammalian ghrelin receptor.

While the invention will be described in conjunction with an example embodiment, it will be understood that it is not intended to limit the scope of the invention to such embodiment. On the contrary, it is intended to cover all alternatives, modifications and equivalents as may be included as defined by the appended claims.

DETAILED DESCRIPTION OF THE INVENTION

Figure 1:
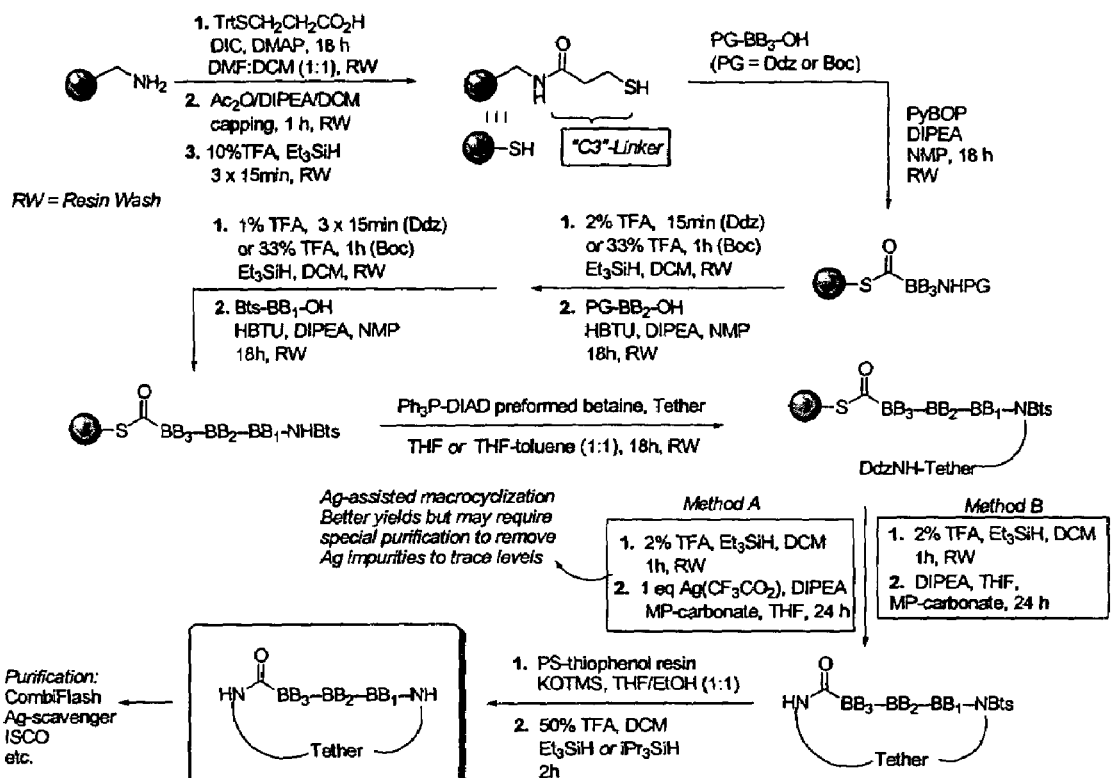
FIG. 1 is a general scheme showing one approach to the solid phase synthesis of compounds of the invention.

The unique compounds of the invention combine four key elements that have never previously been simultaneously investigated:
(1) Recognition potential of amino acid and other functionalized side chains
(2) Conformational rigidity and resistance to degradation of the macrocyclic ring
(3) Modified hydrogen-bonding and polarity, improved stability, and modulated physical properties and recognition potential of peptide bond surrogates which have proven potential in bioactive substances
(4) Spatial control through the non-peptidic tether component The invention also has significant advantages over the existing compounds and libraries for drug discovery:
dramatic improvement in information obtained from testing of the compound libraries since control of conformation through the tether component provides immediate knowledge of bioactive forms;
control of conformation allows defined variation, with different tethers, in the display of those recognition elements to attain the three-dimensional orientation for which ligand-target interactions could be maximized (the tether moiety can actually constrain the cyclic structure into a single low energy conformation in some cases);
high biological relevance through the use of amino acid side chains in the recognition elements ($A_i$) to mimic existing molecular recognition processes between proteins, nucleic acids and proteins, or peptides and proteins;
applicability to broad range of targets and pharmaceutically interesting development of small molecule pharmaceuticals, such as those involving protein-protein or protein-nucleic acid interactions;
utility of the compounds as probes for new and existing protein, enzyme and receptor targets, with particular relevance given the many new targets arising from the efforts in genomics and proteomics;
increased speed in both hit follow-up and lead optimization of bioactive molecules due to basic chemistry assembly method remaining the same, with variations introduced primarily through the individual building units, which can be readily used to modulate and optimize any observed activity;
significant chemical diversity achieved through individual building units that are designed to provide enhanced potential for bioactivity
in the solid phase process for synthesis of these compounds, use of a cleavage-release strategy from resin directly provides compounds biased towards high purity as non-cyclic compounds remain bound to solid support, thereby circumventing the usually lengthy purification process; and
synthetic methods lead to a high degree of synthesis success (>95%) with the ability to be straightforwardly scaled up for larger material quantities since the original methodology was developed as a standard solution phase process.

As such, the compounds of the invention are novel structures with high potential in the search for new bioactive substances with favorable properties.

Accordingly, the invention provides macrocyclic compounds of formulas (I) and (II)

wherein $A_1$, $A_2$, $A_3$, $A_4$, X, T and $T_2$ are as defined previously.

In a preferred embodiment of the macrocyclic compounds of formula (I), T is chosen from the chosen from the group consisting of:

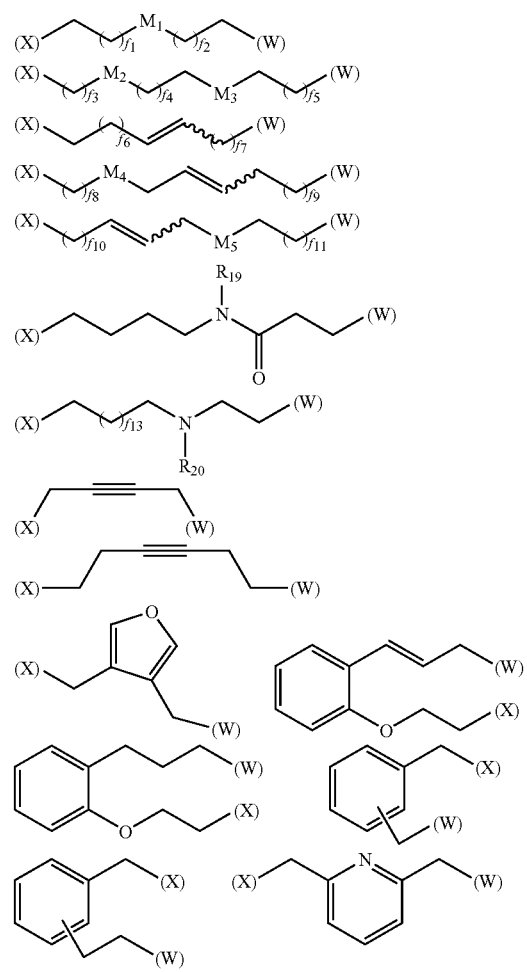

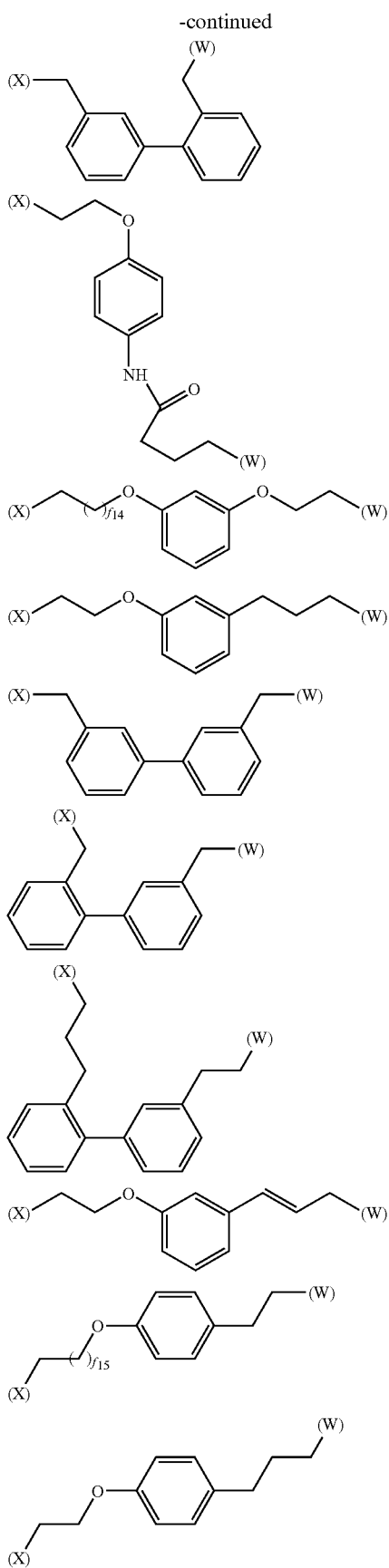

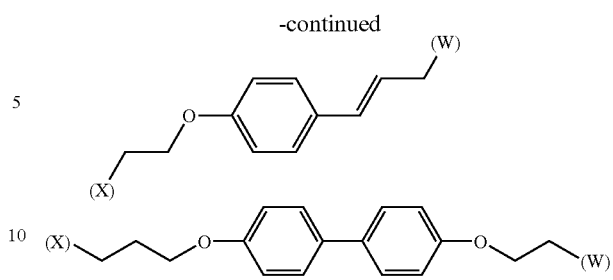

wherein the wavy line indicates a E, Z or a mixture of E and Z double bond configuration;

$M_1$, $M_2$, $M_3$, $M_4$ and $M_5$ are independently selected from O, S or $NR_{18}$ wherein $R_{18}$ is selected from the group consisting of hydrogen, alkyl, substituted alkyl, formyl, acyl and sulfonyl;

$f_1$, $f_2$, $f_4$, $f_7$ and $f_{10}$ are independently selected from 1, 2, 3 or 4;

$f_3$ and $f_8$ are independently selected from 2 or 3;

$f_5$, $f_{11}$, $f_{13}$, $f_{14}$ and $f_{15}$ are independently selected from 1 or 2;

$f_6$ is 0, 1, 2, 3 or 4; and $f_9$ is 0, 1 or 2;

(X) indicates the point of attachment of T to X; and (W) indicates the point of attachment of T to $A_2$, $A_3$ or $A_4$.

In a specific embodiment of the compound of formula (I), T is chosen from the group consisting of:

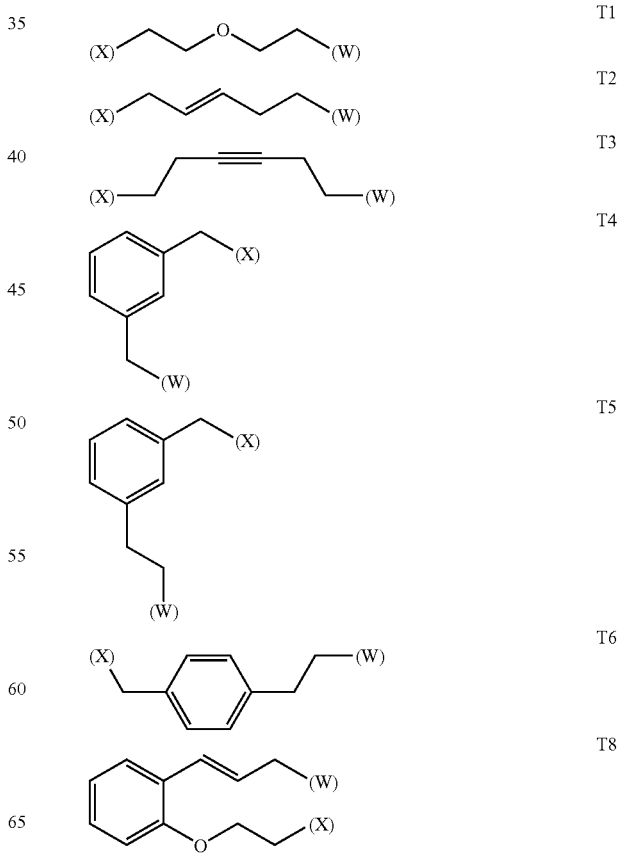

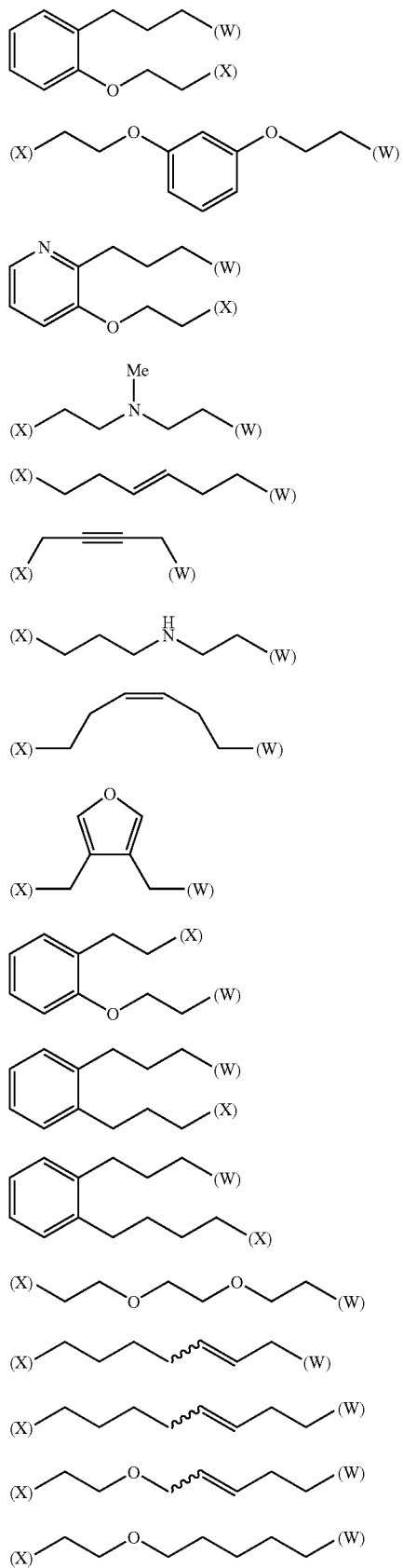
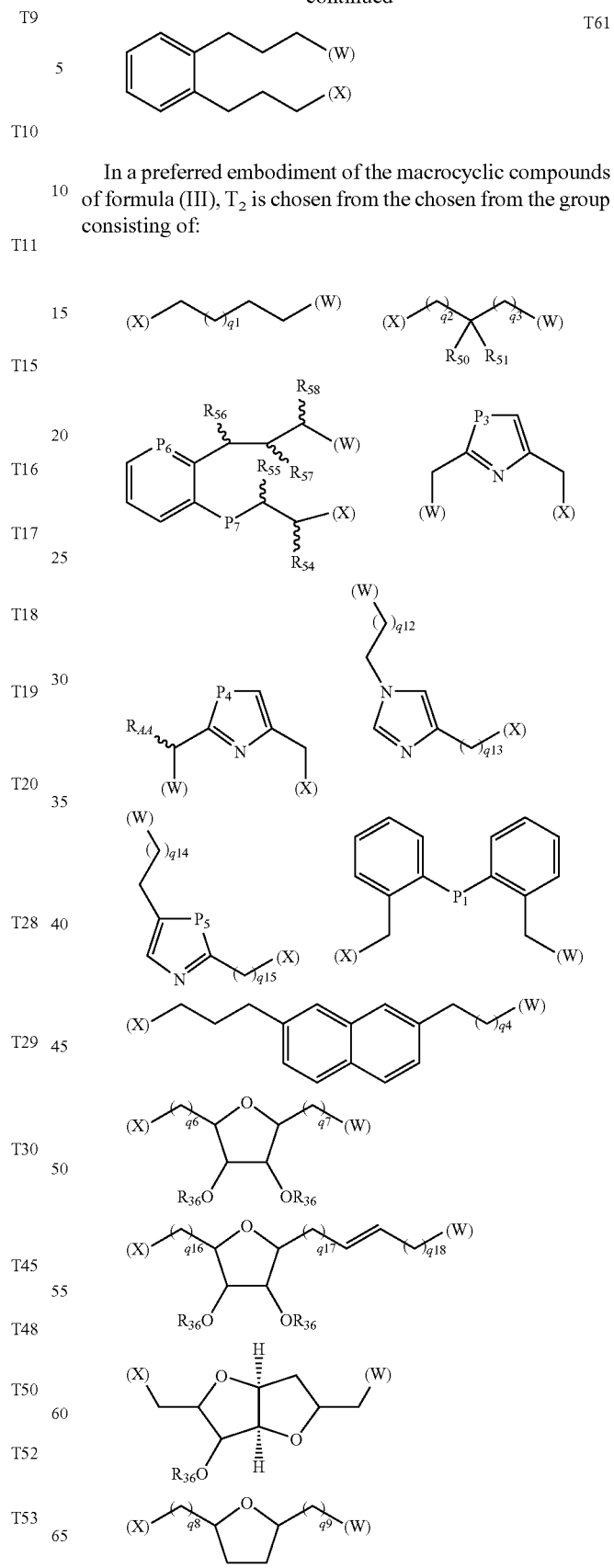
In a preferred embodiment of the macrocyclic compounds of formula (III), $T_2$ is chosen from the chosen from the group consisting of:

-continued

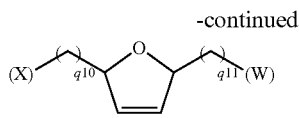

wherein the wavy lines indicate either a (R) or (S) stereochemistry or mixture thereof;

$q_1$, $q_2$, $q_3$, $q_6$, $q_7$, $q_8$, $q_9$, $q_{10}$, $q_{11}$, $q_{13}$, $q_{15}$ and $q_{16}$ are each independently 1, 2, 3, 4 or 5;

$q_4$ and $q_{18}$ are independently 1 or 2;

$q_{12}$ and $q_{14}$ are each independently 0, 1, 2, 3 or 4;

$q_{17}$ is 0, 1, 2 or 3;

$P_1$, $P_3$ $P_4$ and $P_5$ are each independently O, S or NH;

$P_6$ is N or CH;

$P_7$ is O or $CR_{52}R_{53}$;

$R_{36}$ is hydrogen, $C_1$-$C_6$ alkyl, benzyl or acyl;

$R_{50}$ and $R_{51}$ are independently selected from the group consisting of hydrogen, alkyl, hydroxy, alkoxy, and amino with the proviso that if one of $R_{50}$ or $R_{51}$ is hydroxy, alkoxy or amino, the other is hydrogen or alkyl;

$R_{52}$ and $R_{53}$ are independently selected from the group consisting of hydrogen, alkyl, hydroxy, alkoxy, and amino with the proviso that if one of $R_{52}$ or $R_{53}$ is hydroxyl, alkoxy or amino, the other is hydrogen or alkyl;

$R_{54}$, $R_{55}$, $R_{56}$, $R_{57}$ and $R_{58}$ are independently selected from the group consisting of hydrogen, alkyl, hydroxy, alkoxy, and amino;

$R_{AA}$ is the side chain of a natural amino acid;

(X) indicates the point of attachment of T to X; and (W) indicates the point of attachment of T to $A_2$, $A_3$ or $A_4$.

In yet another specific embodiment of the compound of formula (III), $T_2$ is chosen from the group consisting of:

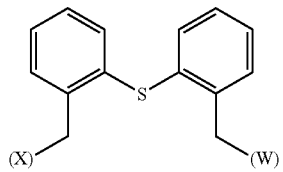
T12

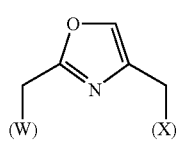
T13

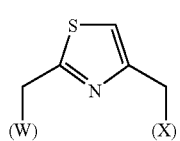
T14

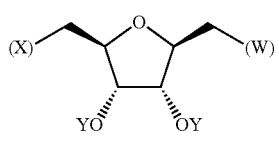
T21

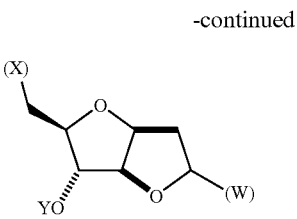
T22

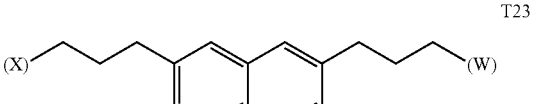
T23

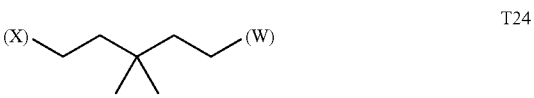
T24

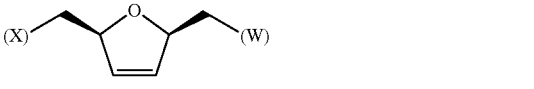
T26

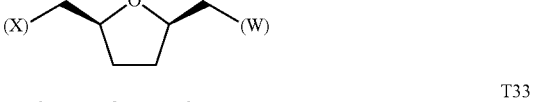
T27

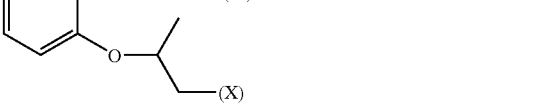
T33

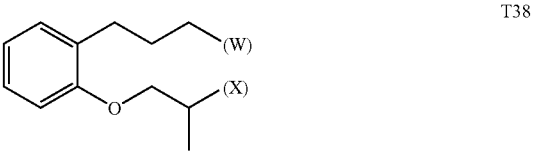
T38

T39

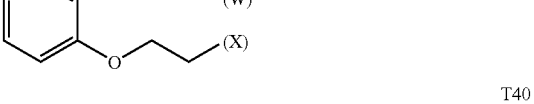
T40

T41

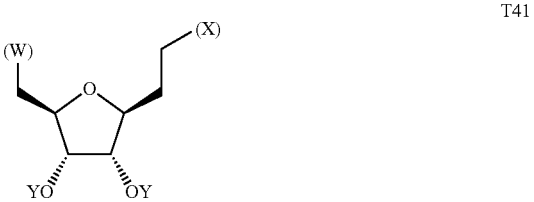
T43

-continued

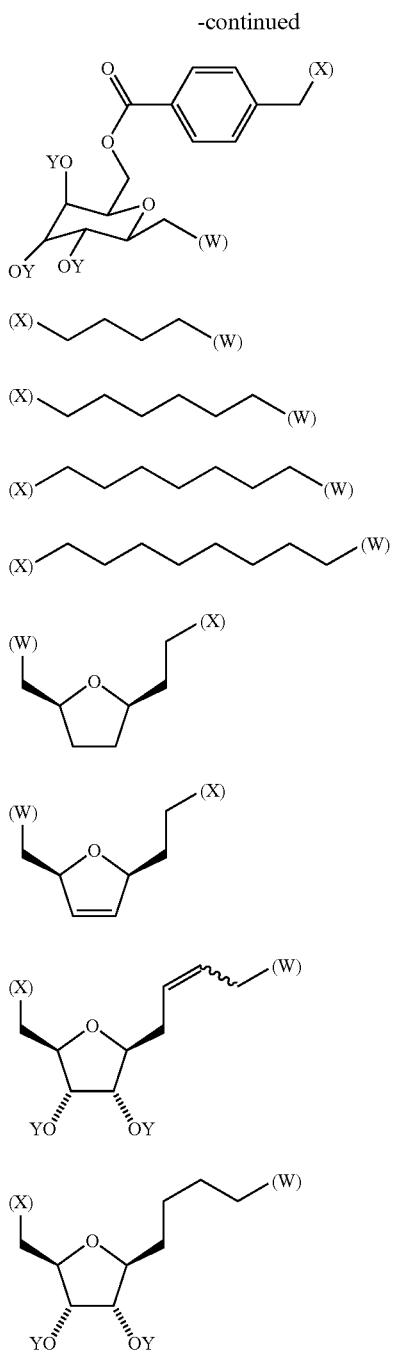

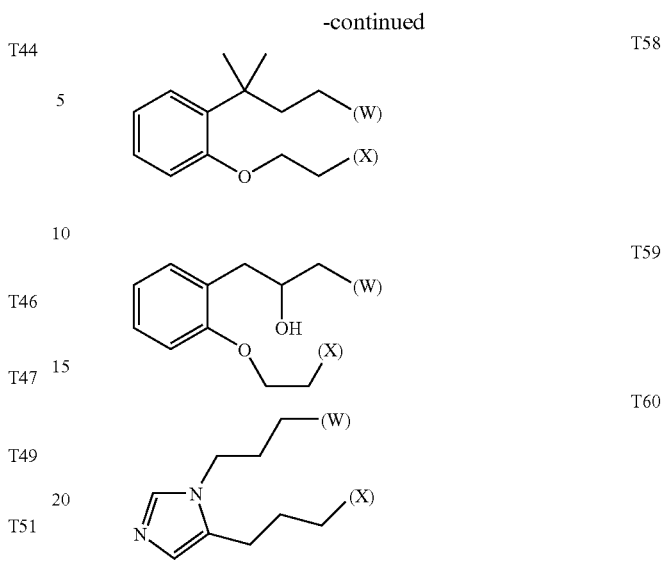

wherein Y is selected from hydrogen, alkyl, benzyl or acyl

The invention also provides compounds of formula (I) and formula (III) which are agonists or antagonists of a mammalian motilin receptor and/or a mammalian ghrelin receptor.

Motilin, a linear 22-amino acid peptide, plays a critical regulatory role in the GI physiological system through governing of fasting gastrointestinal motor activity. As such, the peptide is periodically released from the duodenal mucosa during fasting in mammals, including humans. More precisely, motilin exerts a powerful effect on gastric motility through the contraction of gastrointestinal smooth muscle to stimulate gastric emptying, decrease intestinal transit time and initiate phase III of the migrating motor complex in the small bowel. Due to the critical and direct involvement of motilin in control of gastric motility, agents that either diminish (hypomotility) or enhance (hypermotility) the activity at the motilin receptor, are a particularly attractive area for further investigation in the search for new effective pharmaceuticals towards these indications. Macrocyclic antagonists of the motilin receptor are disclosed in U.S. Prov. Pat. Appl. Ser. No. 60/479,223.

Likewise, ghrelin is a key peptide hormone involved in a number of important physiological functions including growth hormone secretion, maintenance of energy balance, appetite and gut motility. As such, antagonists of this receptor have been investigated for treatment of obesity, while ghrelin agonists have interest in treatment of a variety of diseases, including conditions caused by growth hormone deficiency, wasting syndrome, and GI disorders involving dysmotility.

```
Phe-Val-Pro-Ile-Phe-Thr-Tyr-Gly-Glu-Leu-Gln-Arg-Met-Gln-Glu-Lys-    motilin (human, porcine, SEQ ID NO:1)
Glu-Arg-Asn-Lys-Gly-Gln Gly-Ser-Ser(Oct)-Phe-Leu-Ser-Pro-Glu-His-Gln-Arg-Val-Gln-Gln-Arg-   ghrelin (human SEQ ID NO:2)
Lys-Glu-Ser-Lys-Lys-Pro-Pro-Ala-Lys-Leu-Gln-Pro-Arg
```

EXAMPLES

Table 1A and 1B give the structure of 69 compounds according to the invention. Table 2 lists the mass spectral analytical data for these 69 compounds.

TABLE 1A

Representative Compounds of formula (I)

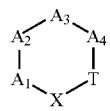

X is NH, except for compound 167 where X is
NMe and compound 168 where X is NAc

| Compound | A₁ | A₂ | A₃ | T |
|---|---|---|---|---|
| 101 | 3-chlorobenzyl substituted | isopropyl (valine-like) | guanidinyl-methyl | T9 |
| 102 | 3-chlorobenzyl with vinyl | isopropyl | dimethylaminomethyl | T9 |
| 103 | 3-chlorobenzyl amide | isopropyl | ethyl (sec-butyl amide) | T9 |
| 104 | 3-chlorobenzyl amide with vinyl | isopropyl with vinyl | ethyl amide | T9 |
| 105 | 4-methoxybenzyl with vinyl | isopropyl | ethyl amide | T9 |
| 106 | 4-methoxybenzyl with CH₂NH | isopropyl | ethyl amide | T9 |

TABLE 1A-continued

Representative Compounds of formula (I)

X is NH, except for compound 167 where X is NMe and compound 168 where X is NAc

| Compound | A₁ | A₂ | A₃ | T |
|---|---|---|---|---|
| 107 | MeO-C₆H₄-CH₂-CH(-)-CH₂-NH- | -CH(iPr)-C(=O)-NH- | -CH(nPr)-C(=O)-NH- | T9 |
| 108 | MeO-C₆H₄-CH₂-CH(-)-CH=CH- | -CH(iPr)-C(=O)-NH- | -CH(nPr)-C(=O)-NH- | T9 |
| 109 | MeO-C₆H₄-CH₂-CH(-)-CH₂-CH₂- | -CH(iPr)-C(=O)-NH- | -CH(nPr)-C(=O)-NH- | T9 |
| 110 | MeO-C₆H₄-CH₂-CH(-)-CH₂-CH₂- | -CH(iPr)-C(=O)-NH- | -CH(nPr)-C(=O)-NH- | T9 |
| 111 | naphthyl-CH₂-CH(-)-C(=O)-O- | -CH(iPr)-C(=O)-NH- | -CH(nPr)-C(=O)-NH- | T9 |
| 112 | MeO-C₆H₄-CH₂-CH(-)-C(=O)-O- | -CH(iPr)-C(=O)-NH- | -CH(nPr)-C(=O)-NH- | T9 |

TABLE 1A-continued
Representative Compounds of formula (I)
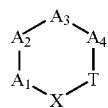
(I)
X is NH, except for compound 167 where X is
NMe and compound 168 where X is NAc
| Compound | $A_1$ | $A_2$ | $A_3$ | T |
|---|---|---|---|---|
| 113 | naphthylmethyl | val | N-Me urea | T61 |
| 114 | naphthylmethyl | val | urea | T54 |
| 115 | 4-hydroxybenzyl | val | ester | T9 |
| 116 | 4-hydroxybenzyl | N-Me val | leu | T9 |
| 117 | 4-hydroxybenzyl | N-Me val | ile | T9 |

TABLE 1A-continued
Representative Compounds of formula (I)
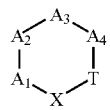
X is NH, except for compound 167 where X is
NMe and compound 168 where X is NAc
| Compound | $A_1$ | $A_2$ | $A_3$ | T |
|---|---|---|---|---|
| 118 | | | | T9 |
| 119 | | | | T9 |
| 120 | | | | T50 |
| 123 | | | | T53 |
| 124 | | | | T9 |

TABLE 1A-continued

Representative Compounds of formula (I)

(I)

X is NH, except for compound 167 where X is NMe and compound 168 where X is NAc

| Compound | A₁ | A₂ | A₃ | T |
|---|---|---|---|---|
| 125 | HO₂C-... | ... | benzyl-... | T9 |
| 126 | ... | ... | benzyl-... | T9 |
| 127 | H₂N-... | ... | benzyl-... | T9 |
| 128 | benzyl-... | ... | benzyl-... | T9 |
| 129 | HO-... | ... | benzyl-... | T9 |
| 130 | ... | ... | benzyl-... | T9 |

TABLE 1A-continued
Representative Compounds of formula (I)
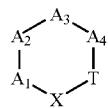
X is NH, except for compound 167 where X is
NMe and compound 168 where X is NAc
| Compound | A₁ | A₂ | A₃ | T |
|---|---|---|---|---|
| 131 | | | | T9 |
| 132 | | | | T9 |
| 133 | | | | T9 |
| 134 | | | | T9 |
| 135 | | | | T9 |

TABLE 1A-continued
Representative Compounds of formula (I)
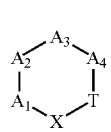
(I)
X is NH, except for compound 167 where X is
NMe and compound 168 where X is NAc
| Compound | A$_1$ | A$_2$ | A$_3$ | T |
|---|---|---|---|---|
| 136 | | | | T9 |
| 137 | | | | T9 |
| 138 | | | | T9 |
| 139 | | | | T9 |
| 140 | | | | T45 |
| 141 | | | | T45 |

TABLE 1A-continued
Representative Compounds of formula (I)
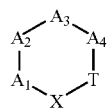
X is NH, except for compound 167 where X is
NMe and compound 168 where X is NAc
| Compound | A₁ | A₂ | A₃ | T |
|---|---|---|---|---|
| 145 | | | | T48 |
| 148 | | | | T50 |
| 149 | | | | T10 |
| 151 | | | | T18 |
| 153 | | | | T2 |

TABLE 1A-continued

Representative Compounds of formula (I)

$$\text{(I)}$$

X is NH, except for compound 167 where X is
NMe and compound 168 where X is NAc

| Compound | A₁ | A₂ | A₃ | T |
|---|---|---|---|---|
| 154 | | | (4-F-phenyl) | T17 |
| 155 | | | (phenyl) | T1 |
| 156 | | | (phenyl) | T3 |
| 157 | | | (phenyl) | T16 |
| 158 | | | (phenyl) | T4 |
| 159 | | | (phenyl) | T5 |

TABLE 1A-continued

Representative Compounds of formula (I)

X is NH, except for compound 167 where X is NMe and compound 168 where X is NAc

| Compound | $A_1$ | $A_2$ | $A_3$ | T |
|---|---|---|---|---|
| 163 | | | | T8 |
| 164 | | | | T9 |
| 165 | | | | T8 |
| 166 | | | | T8 |
| 167 | | | | T9 |
| 168 | | | | T9 |

TABLE 1A-continued

Representative Compounds of formula (I)

X is NH, except for compound 167 where X is NMe and compound 168 where X is NAc

| Compound | A₁ | A₂ | A₃ | T |
|---|---|---|---|---|
| 169 | | | | T9 |
| 170 | | | | T9 |

TABLE 1B

Representative Compounds of formula (III)

X is NH

| Compound | A₁ | A₂ | A₃ | T₂ |
|---|---|---|---|---|
| 121 | | | | T51 |
| 122 | | | | T51 |

TABLE 1B-continued

Representative Compounds of formula (III)

(III)

X is NH

| Compound | A₁ | A₂ | A₃ | T₂ |
|---|---|---|---|---|
| 142 | | | | T46 |
| 143 | | | | T47 |
| 144 | | | | T47 |
| 146 | | | | T49 |
| 147 | | | | T49 |
| 150 | | | | T21 |

TABLE 1B-continued

Representative Compounds of formula (III)

(III)

$$\begin{array}{c} A_3 \\ A_2 \quad A_4 \\ A_1 \quad T_2 \\ X \end{array}$$

X is NH

| Compound | A₁ | A₂ | A₃ | T₂ |
|---|---|---|---|---|
| 152 | (structure) | (structure) | 4-F-benzyl (structure) | T24 |
| 160 | (structure) | (structure) | benzyl (structure) | T12 |
| 161 | (structure) | (structure) | benzyl (structure) | T27 |
| 162 | (structure) | (structure) | benzyl (structure) | T14 |

TABLE 2

Mass Spectral Analysis of Representative Compounds of the Invention

| Compound | Molecular Formula | Molecular Weight | Monoisotopic Mass | MS Found (M + H)⁺ |
|---|---|---|---|---|
| 101 | C30H43N6O3Cl | 571.2 | 570 | 571 |
| 102 | C31H45N4O3Cl | 557.2 | 556 | 557 |
| 103 | C31H44N3O3Cl | 542.2 | 541 | 542 |
| 104 | C31H42N3O3Cl | 540.1 | 539 | 540 |
| 105 | C32H45N3O4 | 535.7 | 535 | 536 |
| 106 | C30H44N4O4 | 524.7 | 524 | 525 |
| 107 | C30H44N4O4 | 524.7 | 524 | 525 |
| 108 | C32H45N3O4 | 535.7 | 535 | 536 |
| 109 | C32H47N3O4 | 537.7 | 537 | 538 |
| 110 | C32H47N3O4 | 537.7 | 537 | 538 |
| 111 | C34H43N3O5 | 573.7 | 573 | 574 |
| 112 | C31H43N3O6 | 553.7 | 553 | 554 |
| 113 | C32H39N5O3 | 541.7 | 541 | 542 |
| 114 | C32H39N5O3 | 541.7 | 541 | 542 |
| 115 | C30H41N3O6 | 539.7 | 539 | 540 |
| 116 | C32H46N4O5 | 566.7 | 566 | 567 |
| 117 | C31H44N4O5 | 552.7 | 552 | 553 |
| 118 | C30H41N3O6 | 539.7 | 539 | 540 |
| 119 | C30H41N3O6 | 539.7 | 539 | 540 |
| 120 | C27H41N3O5 | 487.6 | 487 | 488 |

TABLE 2-continued

Mass Spectral Analysis of Representative Compounds of the Invention

| Compound | Molecular Formula | Molecular Weight | Monoisotopic Mass | MS Found $(M + H)^+$ |
|---|---|---|---|---|
| 121 | C27H43N3O5 | 489.6 | 489 | 490 |
| 122 | C26H39N3O6 | 489.6 | 489 | 490 |
| 123 | C26H41N3O6 | 491.6 | 491 | 492 |
| 124 | C26H34N4O4 | 466.6 | 466 | 467 |
| 125 | C28H36N4O6 | 524.6 | 524 | 525 |
| 126 | C25H32N4O4 | 452.5 | 452 | 453 |
| 127 | C29H41N5O4 | 523.7 | 523 | 524 |
| 128 | C32H38N4O4 | 542.7 | 542 | 543 |
| 129 | C26H34N4O5 | 482.6 | 482 | 483 |
| 130 | C32H46N4O4 | 550.7 | 550 | 551 |
| 131 | C32H46N4O4 | 550.7 | 550 | 551 |
| 132 | C32H46N4O4 | 550.7 | 550 | 551 |
| 133 | C32H46N4O4 | 550.7 | 550 | 551 |
| 134 | C33H48N4O4 | 564.8 | 564 | 565 |
| 135 | C33H48N4O4 | 564.8 | 564 | 565 |
| 136 | C33H48N4O4 | 564.8 | 564 | 565 |
| 137 | C33H48N4O4 | 564.8 | 564 | 565 |
| 138 | C33H48N4O4 | 564.8 | 564 | 565 |
| 139 | C29H40N4O4 | 508.7 | 508 | 509 |
| 140 | C24H35N4O5F | 478.6 | 478 | 479 |
| 141 | C24H35N4O5F | 478.6 | 478 | 479 |
| 142 | C23H35N4O3F | 434.5 | 434 | 435 |
| 143 | C25H39N4O3F | 462.6 | 462 | 463 |
| 144 | C25H39N4O3F | 462.6 | 462 | 463 |
| 145 | C26H40N4O3 | 456.6 | 456 | 457 |
| 146 | C26H42N4O3 | 458.6 | 458 | 459 |
| 147 | C26H42N4O3 | 458.6 | 458 | 459 |
| 148 | C27H42N4O3 | 470.6 | 470 | 471 |
| 149 | C28H35N4O5F | 526.6 | 526 | 527 |
| 150 | C24H33N4O6F | 492.5 | 492 | 493 |
| 151 | C23H34N5O3F | 447.5 | 447 | 448 |
| 152 | C26H41N4O3F | 476.6 | 476 | 477 |
| 153 | C24H35N4O3F | 446.6 | 446 | 447 |
| 154 | C23H31N4O3F | 430.5 | 430 | 431 |
| 155 | C21H32N4O4 | 404.5 | 404 | 405 |
| 156 | C23H32N4O3 | 412.5 | 412 | 413 |
| 157 | C23H34N4O3 | 414.5 | 414 | 415 |
| 158 | C25H32N4O3 | 436.5 | 436 | 437 |
| 159 | C26H34N4O3 | 450.6 | 450 | 451 |
| 160 | C31H36N4O3S | 544.7 | 544 | 545 |
| 161 | C23H34N4O4 | 430.5 | 430 | 431 |
| 162 | C22H29N5O3S | 443.6 | 443 | 444 |
| 163 | C29H41FN4O3 | 512.7 | 512 | 513 |
| 164 | C30H43N4O3F | 526.7 | 526 | 527 |
| 165 | C29H39N5O4 | 521.7 | 521 | 522 |
| 166 | C29H39N5O4 | 521.7 | 521 | 522 |
| 167 | C30H42N4O4 | 522.7 | 522 | 523 |
| 168 | C31H42N4O5 | 550.7 | 550 | 551 |
| 169 | C28H38N4O4 | 494.6 | 494 | 495 |
| 170 | C28H38N4O4 | 494.6 | 494 | 495 |

Notes
1. Molecular formulas and molecular weights (MW) are calculated automatically from the structure via ActivityBase software (IDBS, Guildford, Surrey, UK) or, for MW only, from the freeware program Molecular Weight Calculator v. 6.32
2. M + H obtained from LC-MS analysis
3. All analyses conducted on material after preparative purification Synthesis Method Building blocks for the construction of the compounds of the present invention include amino acids, hydroxyl acids, structures for incorporation of the peptide bond surrogates, and the tethers. Amino and hydroxyl acids are available commercially or synthesized via known procedures. Methods for construction of appropriate building blocks for the peptide surrogates also are establihsed in the art. (*Mini-Rev. Med. Chem.* 2002, 2, 463-473; *Mini-Rev. Med. Chem.* 2002, 2, 447-462; *Curr. Med. Chem.* 2002, 9, 2209-2229; *Curr. Med. Chem.* 2002, 9, 2243-2270; *Curr. Med. Chem.* 2002, 9, 963-978; *Curr. Opin. Chem. Biol.* 2002, 6, 872-877; *Curr. Opin. Chem. Biol.* 1998, 2, 441-452; *Angew. Chem. Int. Ed. Engl.* 1994, 33, 1699; *J. Med. Chem.* 1993, 36, 3039-3049; *J. Org Chem.* 2000, 65, 7667-7675). Synthesis of the specific tether components have been described in WO 01/25257 and U.S. Prov. Pat. Appl. Ser. No. 60/491,248.

An assortment of synthetic strategies can be used to access the macrocyclic compounds of the invention, several of which have already been disclosed in WO 01/25257. or are known in the literature.

Figure 2:
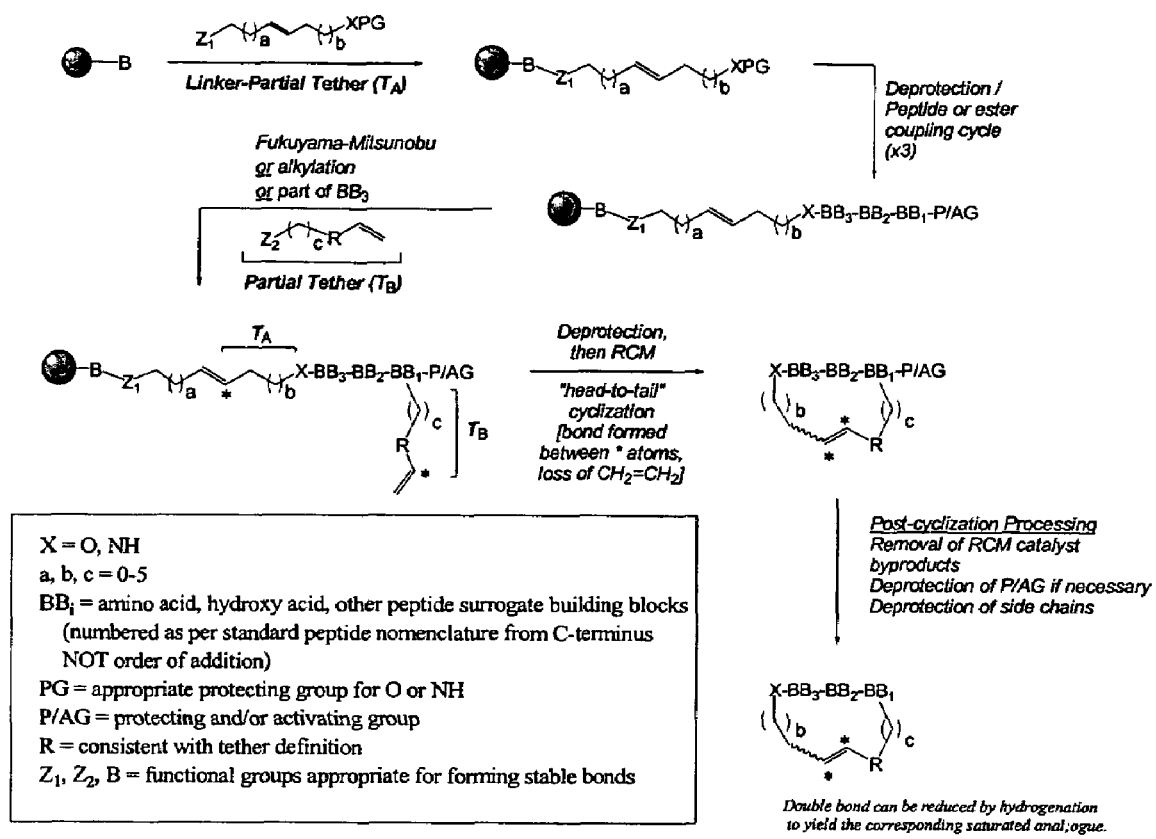
FIG. 2 is a general scheme showing a second approach to the solid phase synthesis of compounds of the invention.
Figure 3:
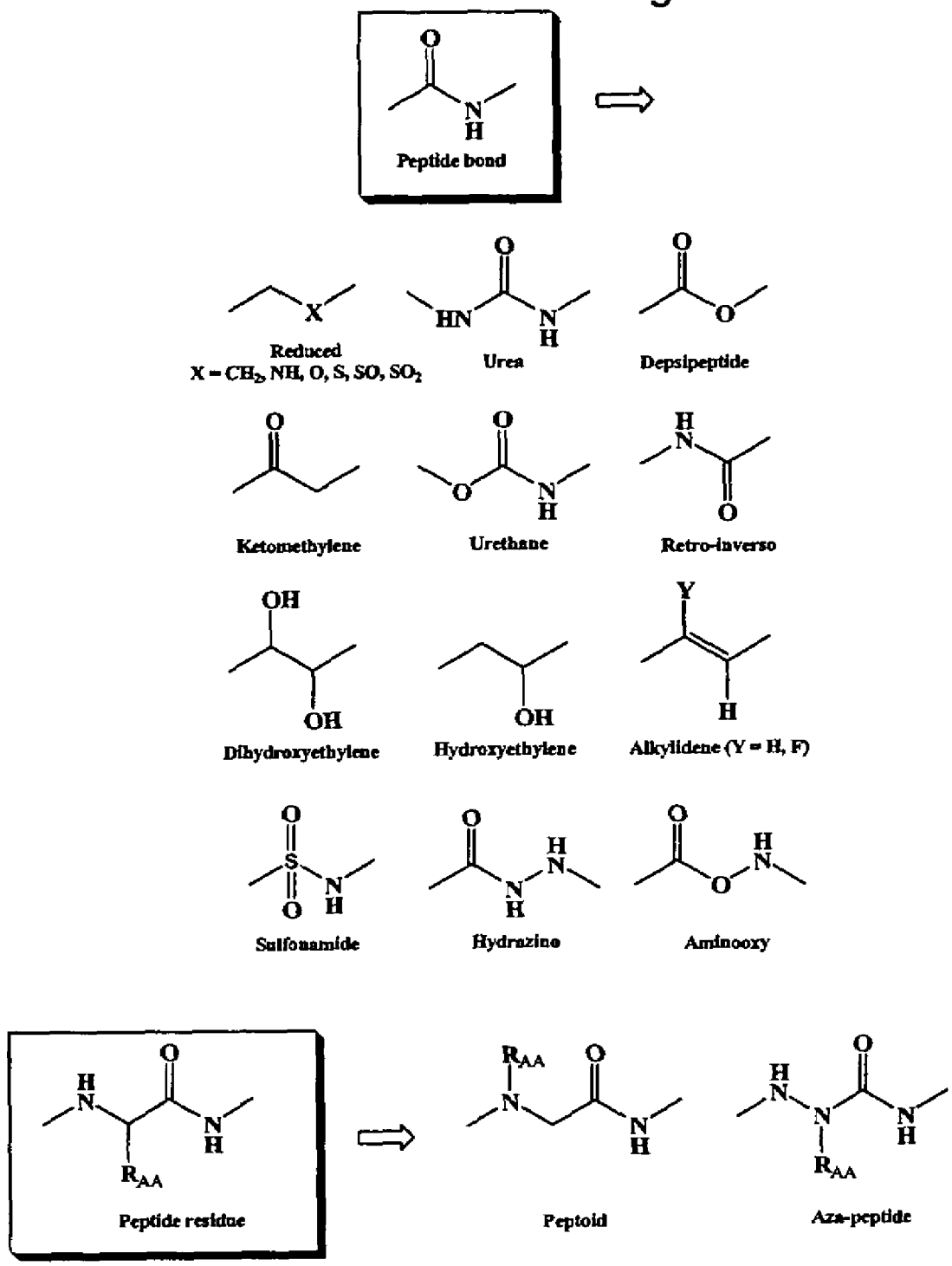
FIG. 3 shows the structures of representative peptide bond surrogates and replacements for peptide residues.

An outline of a first preferred approach to the solid phase synthesis of the compounds of the invention, using a thioester strategy is provided in FIG. 1. A second preferred approach, called ring-closing metathesis (RCM), is also generally outlined in FIG. 2. Yet another alternative approach, utilizing an activated resin for cyclization, is presented in Examples 3 and 4.

Example 1

Representative Synthesis of Macrocyclic Compound of Formula I containing Peptide Surrogate S6

Figure 4A:
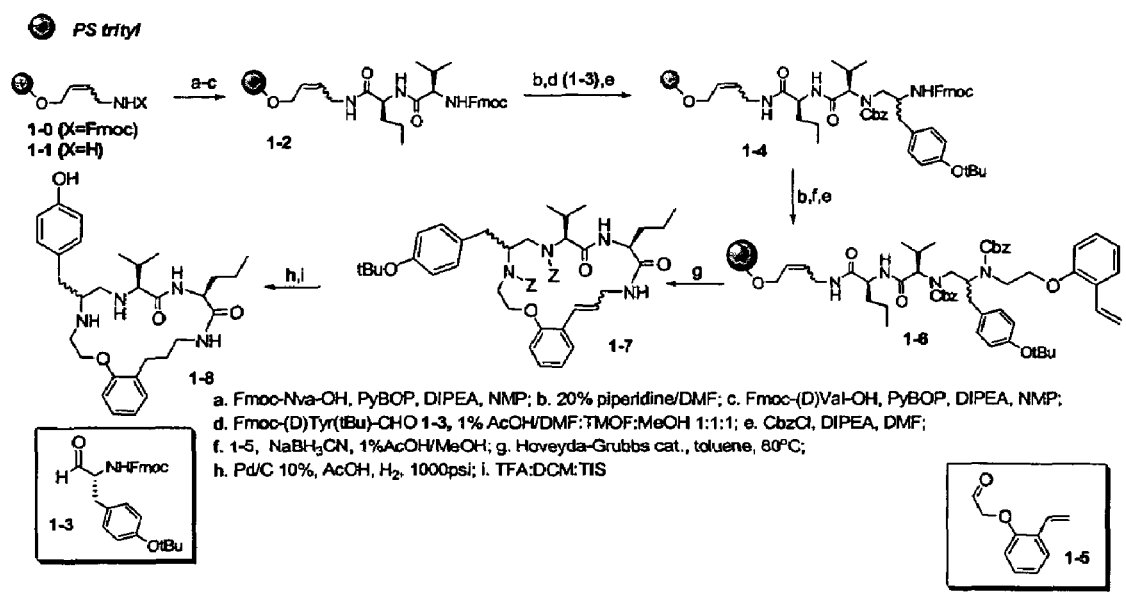
FIGS. 4a-4b, 5a-5b and 6 show synthetic schemes for representative compounds of the invention.
Figure 4:
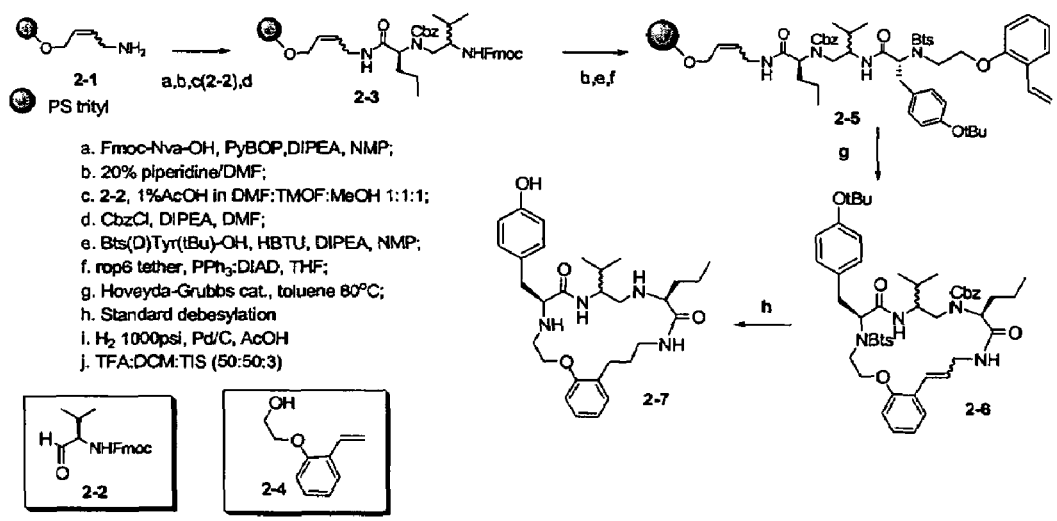

The synthetic scheme is presented as FIG. 4(*a*). Starting from polystyrene trityl resin containing the linker shown (1-0), initial standard Fmoc deprotection of the linker furnished 1-1. This was then coupled with Fmoc Nva-OH under standard conditions. Loading of the resin based upon quantitative analysis of a cleaved aliquot at this stage was 62%. After Fmoc cleavage using standard conditions followed by coupling with Fmoc-(D)Val-OH under standard condition, 1-2 was obtained. After Fmoc group deprotection, reductive alkylation with Fmoc-(D)Tyr(OtBu)-CHO 1-3 was carried out as described in Step 1-d.

Step 1-d: Reductive Amination for Introduction of First Building Block

The following stock solutions were prepared first.
Solution A: 100 mL of 1% AcOH in TMOF (trimethylorthoformate).
Solution B: 100 mL of 1% AcOH in DMF/TMOF/MeOH (1:1:1).

After deprotection of the Fmoc group of 1-2 with 20% piperdine in DMF, 2.0 g (1.5 mmol) of resin were washed 6 times with solution A, dried and transferred into a 100 mL round bottom flask under a $N_2$ atmosphere. Next, 4.6 g (10.5 mmol, 7.0 eq) of aldehyde 1-3 (prepared from the Weinreb amide by LAH reduction using standard methods) were dissolved in 25 mL of solution B and added to the resin. The mixture was stirred at 50° C. for 45 min. To the above mixture was added 1.0 g (15.8 mmol, 10.5 eq) of $NaBH_3CN$ dissolved in 10 mL of solution B. The contents were stirred for an additional 2.5 h at 50° C. The resin was then washed with DMF (5×), then with alternate cycles of DCM/MeOH (2×), DCM (5×) and dried in vacuo.

Step 1-e: Cbz Protection

To the above resin (1.5 mmol) was added 50 mL of DMF (DriSolv® (EMD Chemicals, Inc., part of Merck KGaA, Darmstadt, Germany) grade), followed by 4.0 mL (23 mmol, 15 eq) of DIPEA and 2.1 mL (15 mmol, 10 eq) of CbzCl. The mixture was agitated on an orbital shaker O/N. The resin was then washed with DMF (5×), alternate cycles of DCM/MeOH (4×), DCM (5×) and dried in vacuo.

Step 1-f: Introduction of Partial Tether Component Via Reductive Amination

After cleavage of the Fmoc group using standard conditions, 1.73 g (1.2 mmol) of resin 1-4 was washed with 1% AcOH in MeOH (5×). To the resin was then added a solution of 300 mg (1.8 mmol, 1.5 eq) of 1-5 in 15 mL of MeOH (DriSolv®) and 5 mL of TMOF. This was followed by addition of 0.24 mL (2.4 mmol, 2.0 eq) of NaBH$_3$CN (or BAP) and the reaction was kept on the orbital shaker for 40 h due to the low solubility of 1-5. The resin was washed with MeOH (10×), DMF/MeOH alternate cycles (5×), THF/MeOH alternate cycles (3×), THF (2×), DCM/MeOH alternate cycles (3×), CHCl$_3$ (2×), DCM (4×), then dried in vacuo.

To 1.7 g (1.2 mmol) of the above resin was added 30 mL of DMF (DriSolv®) followed by 2.8 mL (16 mmol, 13 eq) DIPEA and 1.7 mL (12 mmol, 10 eq) of CbzCl. The mixture was agitated O/N. The resin was washed with DMF (5×), DCM/MeOH alternate cycles (3×) and DCM (5×), then dried in vacuo (oil pump). HPLC/MS analysis showed the desired product 1-6 to be formed.

Step 1-g: Macrocyclization Via RCM

RCM was carried out with 1.2 g (0.84 mmol) of 1-6 following the Standard Procedure.

Yield was 102 mg (24%) of the desired macrocycle (1-7) as determined by HPLC/MS/CLND analysis.

Step 1-h: Cbz and Unsaturation Hydrogenation 94 mg (0.11 mmol) of 1-7 was dissolved in 15 mL of glacial AcOH in a 50 mL beaker and 188 mg of 10% Pd/C was added. After degassing, the solution was stirred under 1000 psi of H$_2$ for 7 h. The reaction mixture was then filtered through Celite® (World Minerals Inc., Santa Barbara, Calif.) and the Celite® washed with 10 mL glacial AcOH (2×). The filtrate was then evaporated and the compound dried in vacuo. HPLC/MS analysis verified the identity of the product.

Step 1-i: tBu Group Deprotection

This step was carried out using 50% TFA:50% DCM:3% TIS (triisopropylsilane) for 2 h following standard methods. The crude material was purified by reverse phase preparative HPLC using MS detection to trigger collection of the product (1-8).

Example 2

Representative Synthesis of Macrocyclic Compound of Formula I Containing Peptide Surrogate S6

The synthetic scheme is presented as FIG. 4(b). Anchoring of Fmoc-Nva-OH as well as subsequent Fmoc deprotection were performed following standard procedures. The aldehyde 2-2 from Fmoc-(D)Val-OH was prepared in 62% yield using standard methods. Reductive amination was performed as in step 1-d. Cbz protection of the resulting product under the conditions described in step 1-e (repeated 2×) furnished the desired product 2-3.

Fmoc deprotection, coupling with Bts-(D)Tyr(OtBu)-OH, and Mitsunobu reaction of the resin bound tripeptides surrogate with 2-4 were all carried out under standard conditions to give 2-5. Macrocyclization via RCM with Hoveyda-Grubbs catalyst following the standard procedure furnished the desired product, 2-6. CLND yield: 16.1 mg. Standard deprotection of the Bts group is preferentially performed prior to deprotection of the Cbz group, with simultaneous reduction of the double bond. The final product 2-7 is obtained by deprotection of the tBu group.

Peptide Surrogates S16 or S17

Figure 5A:
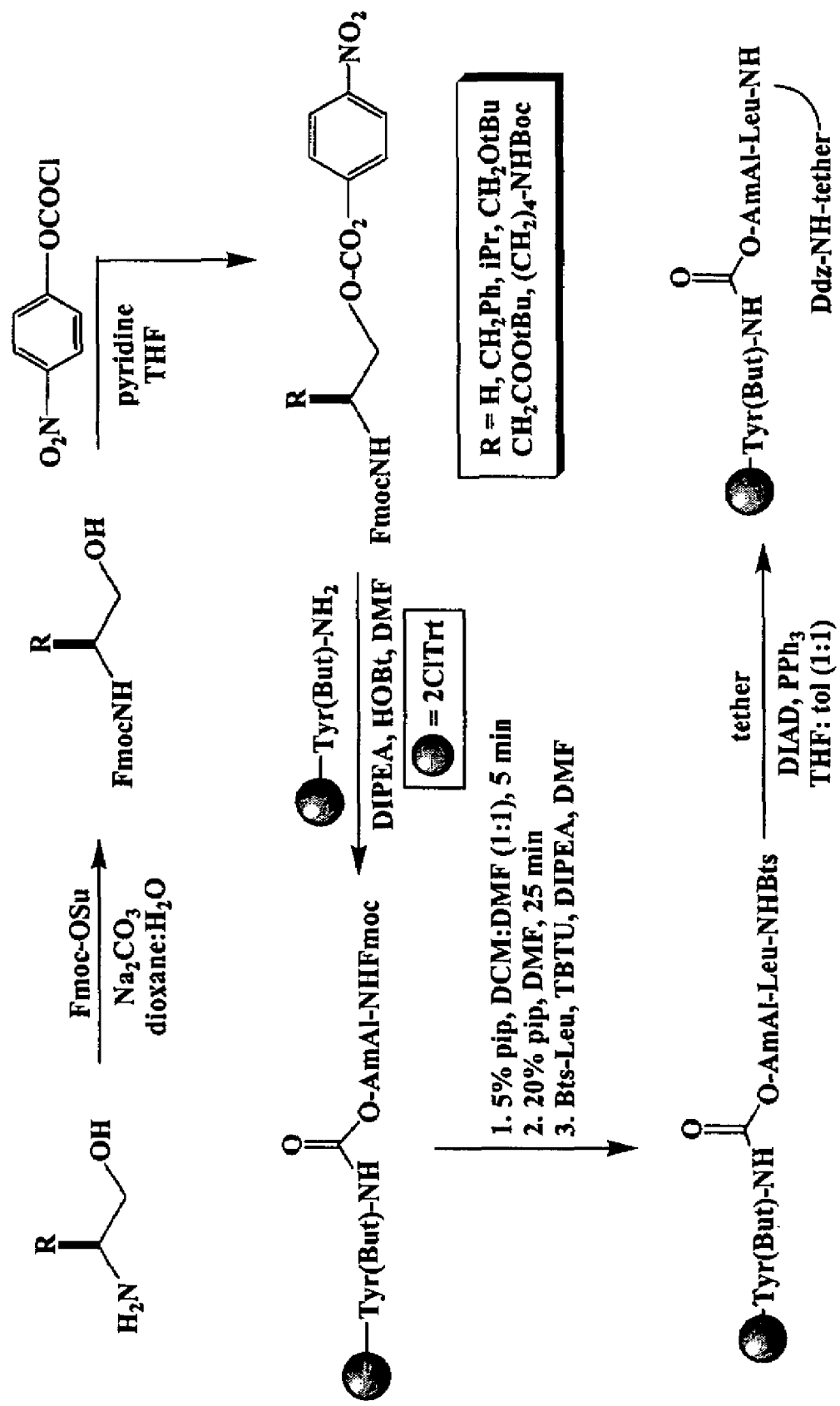
Figure 5B:
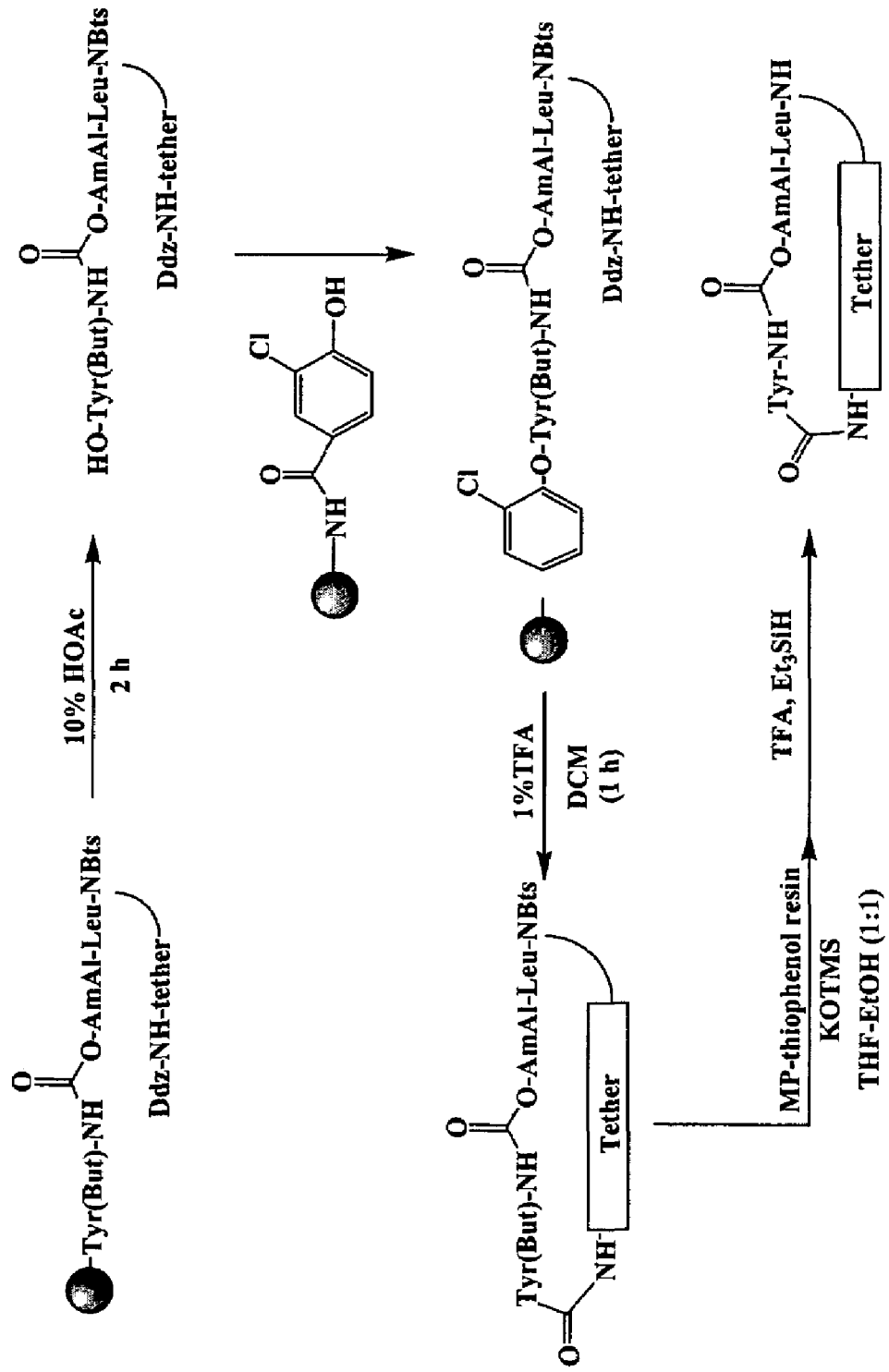

The route presented here offers an alternative route to compounds of the invention as illustrated for the general macrocyclic structure below. FIG. 5 details the reaction sequence as applied to a representative macrocycle containing peptide surrogate S16.

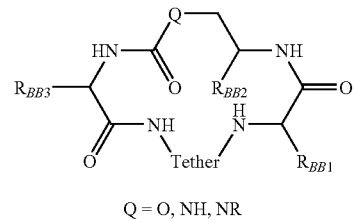

Q = O, NH, NR

Step 3-a: Standard Procedure for Loading Amino Acids to 2-Chlorotrityl Chloride Resin In a 50 mL solid phase reactor, 2-chlorotrityl chloride resin (2 g, 2 mmol/g, 4 mmol) was suspended in DCM (30 mL) and agitated for 15 min. After filtration, a solution of Fmoc-amino acid (4 mmol, 1 eq) and DIPEA (1.75 mL, 10 mmol, 2.5 eq) in DCM (15 mL) was added to the reactor and shaken for 2 h. The resin was filtered and washed with DMF (2×25 mL). (Optionally, but preferably, any remaining active sites on 2-chlorotrityl chloride resin are then capped as follows.) The resin thus obtained was treated with a mixture (25 mL) of DCM:MeOH:DIPEA (80:15:5) for a period of 15 min and then filtered. This treatment was repeated once and the resin finally washed with DMF (3×25 mL) and dried in the standard manner.

Step 3-b: Standard Procedure for Deprotection of Fmoc Protective Groups

The resin from step 3-a was treated with a solution of piperidine in DMF (20%, v/v, 25 mL), agitated for 5 min, then filtered. This process was repeated once, except for 20 min, and the resin finally washed successively with DMF (2×25 mL), iPrOH (2×25 mL), DMF (2×25 mL) and DCM (2×25 mL).

Step 3-c1: Coupling the Fmoc-Protected p-Nitrophenylcarbonate or p-Nitrophenylcarbamate (BB$_2$)

A solution containing the Fmoc-protected amino alcohol or mono-Fmoc-protected diamine derivative (BB$_2$, 0.84 mmol, 4 eq) and HOBt (141 mg, 0.92 mmol, 4.4 eq) in DMF (4 ml) was added to the resin (410 mg, 0.21 mmol) from Step A-2. To this suspension, DIPEA (366 µl, 2.1 mmol, 10 eq) was added and the resulting mixture agitated for 12 h. The resin was filtered, washed sequentially with DMF (2×5 mL), iPrOH (2×5 mL), DMF (2×5 mL), iPrOH (2×5 mL) and DMF (3×5 mL), then dried in the standard manner.

Step 3-c2: Standard Procedure for Coupling Amino Acids using the Fmoc Protection Strategy In other embodiments, an amino acid could be desired in this position. In those instances, this procedure would be employed. To a solution containing the Fmoc (or Ddz)-protected amino acid (BB$_2$, 0.53 mmol, 2.5 eq), and HOBt (121 mg, 0.79 mmol, 3.75 eq) in DMF (2.3 ml) was added DIC (94 µl, 0.58 mmol, 2.50 eq). This solution containing the now activated amino acid was then added to the resin suspension (0.21 mmol, 210 mg) from Step A-2 and agitated for 3 h. The resin was filtered and washed sequentially with DMF (2×5 mL), iPrOH (2×5 mL), DMF (2×5 mL), iPrOH (2×5 mL), DMF (3×5 mL), then dried in the standard manner.

Step 3-d: Removal of Fmoc Protective Group on BB$_2$

The resin was treated as described in step 3-c1, but at 1/5 of the scale therein.

Step 3-e: Coupling of Bts-Amino Acid (BB$_1$)

A solution containing the Bts-amino acid (BB$_1$, 0.42 mmol, 2 eq), TBTU (202 mg, 0.63 mmol, 3 eq) and DIPEA (220 µl, 1.26 mmol, 6 eq) in DMF (2.5 mL) was added to the resin obtained in step 3-d and agitated for 3 h. The resin was filtered and washed sequentially with DMF (2×5 mL), iPrOH (2×5 mL), DMF (2×5 mL), iPrOH (2×5 mL), DMF (3×5 mL), then dried in the standard manner.

Step 3-f: Mitsunobu Reaction

A solution containing the N-protected tether alcohol (0.84 mmol, 4 eq) and triphenylphosphine (220 mg, 0.84 mmol, 4 eq) in a mixture of toluene (2 mL) and tetrahydrofuran (2 mL) was added to the resin obtained in step 3-e. Finally, DIAD (166 µl, 0.84 mmol, 4 eq) was added and the resulting mixture was agitated for 12 h. The resin was filtered, washed sequentially with DMF (2×5 mL), iPrOH (2×5 mL), DCM (4×5 mL) and dried in the standard manner.

Step 3-g: Standard Procedure for Cleavage of the Protected Macrocyclic Precursor from 2-Chlorotrityl Chloride Resin The resin obtained from step 3-f was treated with a mixture of acetic acid:trifluoroethanol:DCM (1:1:8, v/v/v, 5 mL) for 2 h. The resin was filtered and washed once with a fresh 2.5 mL of the 1:1:8 mixture. Toluene (15 mL) was added to the filtrate and the solvents were evaporated under reduced pressure. The alkylated tripeptide to serve as the macrocyclic precursor was thus obtained, usually as a white solid. To confirm the amount, prior to cleavage, an accurate weight of the resin was obtained in order to compare the weight gain observed with the quantity yielded from the cleavage.

Step 3-h: Standard Procedure for Loading Macrocyclic Precursor to Activated Resin A solution containing the alkylated tripeptide (0.05 mmol) in DCM (5 mL) was added to the activated resin, for example TFP resin (213), o-nitrophenyl resin (214), or o-chlorophenyl resin (215) (300 mg). In this case, the latter was employed. Finally, DMAP (1 mg, 0.01 mmol, 0.2 eq) and DIC (23 µl, 0.15 mmol, 3 eq) were added and the suspension was agitated for 12 h. The resin was filtered, washed sequentially with DCM (2×5 mL), THF (2×5 mL), DCM (3×5 mL), then dried in the standard manner.

Step 3-i: Macrocyclization on Activated Resin

The resin obtained from step 3-h was treated with a solution of 2% TFA, 3% TES (or TIPS) in DCM (v/v/v, 5 mL) for 30 min to remove the N-Ddz protecting group of the tether element. The resin was filtered and washed with DCM (2×5 mL). After Ddz deprotection, the resin was treated with a solution 2.5% Dl PEA in THF (5 mL) for 1 h. The basicity of the solution was confirmed during the reaction (wet pH paper) and more DIPEA added if necessary to maintain basicity. The resin was filtered and rinsed with a fresh 2.5 mL of the 2.5% DIPEA in THF solution. The combined filtrate was evaporated under reduced pressure. Precipitation of the macrocycle was induced by adding H$_2$O to the residue. The macrocycle was recovered by filtration and washed with H$_2$O to remove any residual salts. Alternatively, the residue was triturated with H$_2$O.

Step 3-j: The macrocycle obtained in step 3-i was subjected sequentially to the standard deprotection conditions to provide the final macrocycle.

Example 4

Representative Synthesis of Macrocyclic Compound of Formula I containing Peptide Surrogate S3

Figure 6:
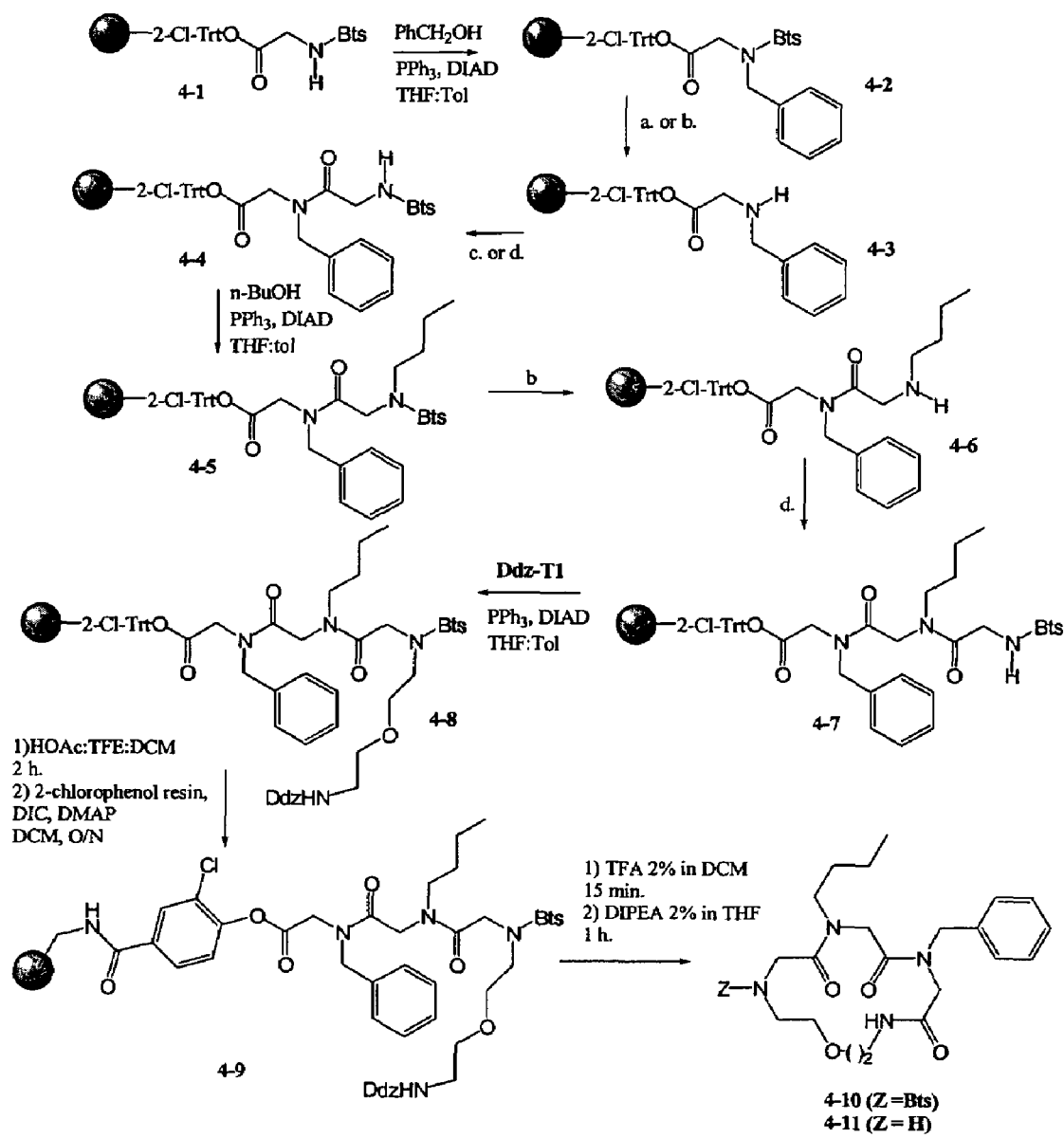

This synthesis is presented in FIG. 6. The protocol highlights an alternative method to those previously reported for introduction of the peptoid moiety.

Step 4-a: In a 500 mL solid phase synthesis reactor was suspended 2-chlorotrityl chloride resin (16.5 g, loading 2.0 mmol/g) in DCM (350 mL). The resulting slurry was agitated for 30 min, filtered and washed with DCM (2×350 mL). Separately, a solution of Bts-Gly-OH (13.4 g, 1.5 eq) and DIPEA (17.2 mL, 3.0 eq) in DCM (350 mL) was prepared to form the Bts-Gly salt. This solution of the carboxylate salt was added to the resin mixture and agitated for an additional 2.5 h. The reaction mixture was filtered and the collected resin washed successively with DMF (3×350 mL), 2-propanol (3×350 mL) and DCM (3×350 mL). Finally, any remaining active sites on the resin were neutralized by treatment with a solution of 85/10/5 DCM/MeOH/DIPEA (350 mL) for 1 h with agitation. The resulting resin was collected by filtration, washed successively with DMF (3×350 mL), 2-propanol (3×350 mL) and DCM (3×350 mL) and dried under vacuum to give 18.73 g of 4-1.

Step 4-b: To the resin 4-1 (1.3 g) was added a solution of benzyl alcohol (538 µl, 4.0 eq) and triphenylphosphine (1.40 g, 4.0 eq) in 10 mL THF and 10 mL of toluene. The resin mixture was agitated for 1 min and then diisopropylazodicarboxylate (DIAD, 1.02 mL, 4.0 eq) is added and agitation continued for 12 h. The resin was collected by filtration, washed successively with DMF (4×25 mL), 2-propanol (3×25 mL) and DCM (4×25 mL) and dried under vacuum to give 4-2.

Step 4-c: To the resin A2 was added a solution of mercaptoethanol (410 µl, 10 eq) and n-propylamine (500 µl, 10 eq) in DMF (9 mL) and the resulting slurry agitated for 3 h. The resin was collected by filtration, washed successively with DMF (3×25 mL), 2-propanol (3×25 mL) and DCM (3×25 mL) and dried under vacuum to provide 4-3.

Step 4-d: To the resin 4-3 was added a solution of Bts-Gly-OH (695 mg, 1.5 eq) and DEBPT (763 mg) in 9.4 mL of DMF. The resin mixture was agitated for 1 min, then DIPEA (666 µl, 2.5 eq) is added and agitation continued for 3 h. The resin was collected by filtration, washed successively with DMF (3×25 mL), 2-propanol (3×25 mL) and DCM (3×25 mL) and dried under vacuum to give 4-4.

Step 4-e: To the resin 4-4 was added a solution of n-butanol (366 µl, 4.0 eq) and triphenylphosphine (1.05 mg, 4.0 eq) in 10 mL THF and 10 mL of toluene. The resin mixture was agitated for 1 min, then DIAD (788 µl, 4.0 eq) is added and agitation continued for 12 h. The resin was collected by filtration, washed successively with DMF (4×25 mL), 2-propanol (3×25 mL) and DCM (4×25 mL) and dried under vacuum to give 4-5.

Step 4-f: To the resin A5 was added a solution of mercaptoethanol (600 µl, 10 eq), n-propylamine (500 µl, 10 eq) in DMF (6 mL) and the resulting slurry agitated for 3 h. The resin was collected by filtration, washed successively with DMF (3×25 mL), 2-propanol (3×25 mL) and DCM (3×25 mL) and dried under vacuum to provide 4-6.

Step 4-g: To the resin 4-6 was added a solution of Bts-Gly-OH (695 mg, 1.5 eq) and DEBPT (763 mg) in 9.4 mL of DMF.

The resin mixture was agitated for 1 min, then DIPEA (666 µl, 2.5 eq) is added and agitation continued for 3 h. The resin was collected by filtration, washed successively with DMF (3×25 mL), 2-propanol (3×25 mL) and DCM (3×25 mL) and dried under vacuum to give 4-7.

Step 4-h: To the resin 4-7 was added a solution of Ddz-T1 (1.3 g, 4.0 eq) and triphenylphosphine (1.05 g, 4.0 eq) in 10 mL THF and 10 mL of toluene. The resin mixture was agitated for 1 min, then DIAD (788 µl, 4.0 eq) is added and agitation continued for 12 h. The resin was collected by filtration, washed successively with DMF (4×25 mL), 2-propanol (3×25 mL) and DCM (4×25 mL) and dried under vacuum to give 4-8.

Step 4-i: To the resin 4-8 was added 10 mL of a solution of AcOH/TFE/DCM (1/1/8) and agitated for 2 h. The resin is filtered and washed with DCM (3×10 mL). The filtrate is evaporated to dryness and the residue further dried under high vacuum. The residual cleaved product is dissolved in 4 mL of DCM, added to the 2-chlorophenyl resin (450 mg), DIC (150 µl) and DMAP (15 mg) and agitated overnight. The resin is washed with DCM (3×), then dried under vacuum to give 4-9.

Step 4-j: To the resin 4-9 was added 5 mL of a solution of 3% TFA in DCM and the resulting slurry agitated for 15 min. The resin is filtered, the treatment repeated once, then the resin washed with DCM (3×5 mL) and dried under vacuum. To the dried resin was added 5 mL of a solution of 2.5% DIPEA in THF and agitated for 1 h. The resin is filtered and washed with THF (3×5 mL). The filtrate is evaporated under reduced pressure and the residue dried under vacuum to yield the macrocycle 4-10.

Step 4-k: The Bts group of 4-10 was removed using standard conditions to provide the final, fully deprotected macrocycle, 4-11. This compound could be further purified by the standard methods.

Biological Evaluation for Compounds of the Invention

The compounds of the present invention were evaluated for their ability to interact at the human motilin receptor and the human ghrelin receptor utilizing competitive radioligand binding assays as described in Method B1 and B2, respectively. Further characterization of the interaction can be performed utilizing the functional assays described in Methods B3 and B4 for the motilin and ghrelin receptors, respectively. All of these methods can be conducted, if so desired, in a high throughput manner to permit the simultaneous evaluation of many compounds.

Results for the examination of representative compounds of the present invention using Methods B1 and B2 are presented in Table 3.

Example Method B1

Competitive Radioligand Binding Assay (Motilin Receptor)

Materials:
  Membranes were prepared from CHO cells stably transfected with the human motilin receptor and utilized at a quantity of 1.5 µg/assay point. [PerkinElmer® SignalScreen® Product #6110544, Perkin Elmer, Inc., Wellesley, Mass.]
  [$^{125}$I]-Motilin (PerkinElmer®, #NEX-378); final concentration: 0.04-0.06 nM
  Motilin (Bachem®, #H-4385, Bachem AG Corporation, Bubendorf, Switzerland); final concentration: 1 µM
  Multiscreen® Harvest plates-GF/B (Millipore®, #MAHFB1H60, Millipore Corporation, Billerica, Mass.)
  Deep-well polypropylene titer plate (Beckman Coulter®, #267006, Beckman Coulter, Inc., Fullerton, Calif.)
  TopSeal-A (PerkinElmer®, #6005185)
  Bottom seal (Millipore®, #MATAH0P00)
  MicroScint™-0 (PerkinElmer®, #6013611)
  Binding Buffer: 50 mM Tris-HCl (pH 7.4), 10 mM $MgCl_2$, 1 mM EDTA, 0.1% BSA Assay Volumes:
  150 µl of membranes diluted in binding buffer
  10 µl of compound diluted in binding buffer
  10 µl of radioligand ([$^{125}$I]-Motilin) diluted in binding buffer
  Final Test Concentrations (N=11) for Compounds: 10, 5, 2, 1, 0.5, 0.2, 0.1, 0.05, 0.02, 0.01, 0.005 µM.

Compound Handling:

Compounds were provided frozen on dry ice at a stock concentration of 10 mM diluted in 100% DMSO and stored at −20° C. until the day of testing. On the test day, compounds were allowed to thaw at room temperature and than diluted in assay buffer according to the desired test concentrations. Under these conditions, the maximum final DMSO concentration in the assay was 0.5%.

Assay Protocol:

In deep-well plates, diluted cell membranes (1.5 µg/mL) are combined with 10 µl of either binding buffer (total binding, N=5), 1 µM motilin (non-specific binding, N=3) or the appropriate concentration of test compound. The reaction is initiated by addition of 10 µl of [$^{125}$I]-motilin (final conc. 0.04-0.06 nM) to each well. Plates are sealed with TopSeal-A, vortexed gently and incubated at room temperature for 2 hours. The reaction is arrested by filtering samples through pre-soaked (0.3% polyethyleneimine, 2 h) Multiscreen® Harvest plates using a Tomtec ® Harvester (TomTec, Inc., Hamden Conn.), washed 9 times with 500 µl of cold 50 mM Tris-HCl (pH 7.4), and than plates are air-dried in a fumehood for 30 minutes. A bottom seal is applied to the plates prior to the addition of 25 µl of MicroScint™-0 to each well. Plates are than sealed with TopSeal-A and counted for 30 sec per well on a TopCount® Microplate Scintillation and Luminescence Counter (PerkinElmer®) where results are expressed as counts per minute (cpm).

Data are analyzed by GraphPad Prism® (GraphPad Software, Inc., San Diego, Calif.) using a variable slope non-linear regression analysis. $K_i$ values were calculated using a $K_d$ value of 0.16 nM for [$^{125}$I]-motilin (previously determined during membrane characterization).

$$D_{max} = 1 - \frac{\text{test concentration with maximal displacement} - \text{non-specific binding}}{\text{total binding} - \text{non-specific binding}} \times 100$$

where total and non-specific binding represent the cpm obtained in the absence or presence of 1 μM motilin, respectively.

Example Method B2

Competitive Radioligand Binding Assay (Ghrelin Receptor)

The competitive binding assay at the human growth hormone secretagogue receptor (hGHS-R1a) was carried out analogously to assays described in the literature. (Bednarek M A et al. (2000), Structure-function studies on the new growth hormone-releasing peptide ghrelin: minimal sequence of ghrelin necessary for activation of growth hormone secretagogue receptor 1a; J Med Chem 43:4370-4376. Palucki B L et al. (2001), Spiro(indoline-3,4'-piperidine) growth hormone secretagogues as ghrelin mimetics; Bioorg Med Chem Lett 11:1955-1957.)

Materials
- Membranes (GHS-R/HEK 293) were prepared from HEK-293 cells stably transfected with the human ghrelin receptor (hGHS-R1a). These membranes were provided by PerkinElmer® BioSignal® (#RBHGHSM, lot#1887) (PerkinElmer BioSignal, Inc. Quebec, Canada) and utilized at a quantity of 0.71 μg/assay point.
- [$^{125}$I]-Ghrelin (PerkinElmer®, #NEX-388); final concentration: 0.0070-0.0085 nM
- Ghrelin (Bachem®, #H-4864); final concentration: 1μM
- Multiscreen® Harvest plates-GF/C (Millipore®, #MAHFC1H60)
- Deep-well polypropylene titer plate (Beckman Coulter®, #267006)
- TopSeal-A (PerkinElmer®, #6005185)
- Bottom seal (Millipore®, #MATAH0P00)
- MicroScint™-0 (PerkinElmer, #6013611)
- Binding Buffer: 25 mM Hepes (pH 7.4), 1 mM CaCl$_2$, 5 mM MgCl$_2$, 2.5 mM EDTA, 0.4% BSA Assay Volumes Competition experiments were performed in a 300 μl filtration assay format.
- 220 μl of membranes diluted in binding buffer
- 40 μl of compound diluted in binding buffer
- 40 μl of radioligand ([$^{125}$I]-Ghrelin) diluted in binding buffer Final test concentrations (N=1) for compounds of the present invention: 10, 1, 0.5, 0.2, 0.1, 0.05, 0.02, 0.01, 0.005, 0.002, 0.001 μM.

Compound Handling

Compounds were provided frozen on dry ice at a stock concentration of 10 mM diluted in 100% DMSO and stored at −80° C. until the day of testing. On the test day, compounds were allowed to thaw at rt overnight and then diluted in assay buffer according to the desired test concentrations. Under these conditions, the maximal final DMSO concentration in the assay was 0.1%.

Assay Protocol

In deep-well plates, 220 μl of diluted cell membranes (final concentration: 0.71 μg/well) were combined with 40 μl of either binding buffer (total binding, N=5), 1 μM ghrelin (non-specific binding, N=3) or the appropriate concentration of test compound (N=2 for each test concentration). The reaction was initiated by addition of 40 μl of [$^{125}$I]-ghrelin (final conc. 0.0070-0.0085 nM) to each well. Plates were sealed with TopSeal-A, vortexed gently and incubated at rt for 30 min. The reaction was arrested by filtering samples through Multiscreen® Harvest plates (pre-soaked in 0.5% polyethyleneimine) using a Tomtec® Harvester, washed 9 times with 500 μL of cold 50 mM Tris-HCl (pH 7.4, 4° C.), and then plates were air-dried in a fumehood for 30 min. A bottom seal was applied to the plates prior to the addition of 25 μl of MicroScint™-0 to each well. Plates were than sealed with TopSeal-A and counted for 30 sec per well on a TopCount® Microplate Scintillation and Luminescence Counter (PerkinElmer®) using a count delay of 60 sec. Results were expressed as counts per minute (cpm).

Data were analyzed by GraphPad Prism® (GraphPad Software, Inc., San Diego, Calif.) using a variable slope non-linear regression analysis. $K_i$ values were calculated using a $K_d$ value of 0.01 nM for [$^{125}$I]-ghrelin (previously determined during membrane characterization).

$D_{max}$ values were calculated using the following formula:

$$D_{max} = 1 - \frac{\text{test concentration with maximal displacement} - \text{non-specific binding}}{\text{total binding} - \text{non-specific binding}} \times 100$$

where total and non-specific binding represent the cpm obtained in the absence or presence of 1 μM ghrelin, respectively.

Example Method B3

Aequorin Functional Assay (Motilin Receptor)

Materials:
- Membranes were prepared using AequoScreen® (EUROSCREEN S A, Belgium) cell lines expressing the human motilin receptor (cell line ES-380-A; receptor accession #AF034632). This cell line is constructed by transfection of the human motilin receptor into CHO-K1 cells co-expressing $G_{\alpha 16}$ and the mitochondrially targeted Aequorin(Ref#ES-WT-A5).
- Motilin (Bachem®, #H-4385)
- Assay buffer: DMEM-F12 (Dulbeccoe's Modified Eagles Medium) with 15 mM HEPES and 0.1% BSA (pH 7.0)
- Coelenterazine (Molecular Probes®, Leiden, The Netherlands)

Compound Handling:

Compounds were provided as dry films at a quantity of approximately 1.2 μmol in pre-formatted 96-well plates. Compounds were dissolved in 100% DMSO at a concentration of 10 mM and stored at −20° C. until further use. Daughter plates were prepared at a concentration of 500 μM in 30% DMSO with 0.1% BSA and stored at −20° C. until testing. On the test day, compounds were allowed to thaw at room temperature and than diluted in assay buffer according to the desired test concentrations. Under these conditions, the maximum final DMSO concentration in the assay was 0.6%.

Cell Preparation:

Cells are collected from culture plates with Ca$^{2+}$ and Mg$^{2+}$-free phosphate buffered saline (PBS) supplemented with 5 mM EDTA, pelleted for 2 minutes at 1000×g, resuspended in assay buffer (see above) at a density of 5×10$^6$ cells/mL and incubated overnight in the presence of 5 μM coelenterazine. After loading, cells were diluted with assay buffer to a concentration of 5×10$^5$ cells/mL.

Assay Protocol:

For agonist testing, 50 µl of the cell suspension was mixed with 50 µl of the appropriate concentration of test compound or motilin (reference agonist) in 96-well plates (duplicate samples). The emission of light resulting from receptor activation was recorded using the Functional Drug Screening System 6000 'FDSS 6000' (Hamamatsu® Photonics K.K., Japan).

For antagonist testing, an approximate EC80 concentration of motilin (i.e. 0.5 nM; 100 µl) was injected onto the cell suspension containing the test compounds (duplicate samples) 15-30 minutes after the end of agonist testing and the consequent emission of light resulting from receptor activation was measured as described in the paragraph above.

Results are expressed as Relative Light Units (RLU). Concentration response curves were analyzed using GraphPad Prism® (GraphPad Software, Inc., San Diego, Calif.) by non-linear regression analysis (sigmoidal dose-response) based on the equation $E=E_{max}/(1+EC_{50}/C)n$ where E is the measured RLU value at a given agonist concentration (C), $E_{max}$ is the maximal response, $EC_{50}$ is the concentration producing 50% stimulation and n is the slope index. For agonist testing, results for each concentration of test compound were expressed as percent activation relative to the signal induced by motilin at a concentration equal to the $EC_{80}$ (i.e. 0.5 nM). For antagonist testing, results for each concentration of test compound were expressed as percent inhibition relative to the signal induced by motilin at a concentration equal to the $EC_{80}$ (i.e. 0.5 nM).

Example Method B4

Aequorin Functional Assay (Ghrelin Receptor)

Materials
  Membranes were prepared using AequoScreen® (EUROSCREEN SA, Belgium) cell lines expressing the human ghrelin receptor (cell line ES-410-A; receptor accession #60179). This cell line is constructed by transfection of the human ghrelin receptor into CHO-K1 cells co-expressing $G_{\alpha16}$ and the mitochondrially targeted Aequorin (Ref#ES-WT-A5).
  Ghrelin (reference agonist; Bachem®, #H-4864)
  Assay buffer: DMEM (Dulbecco's Modified Eagles Medium) containing 0.1% BSA (bovine serum albumin; pH 7.0.
  Coelenterazine (Molecular Probes®, Leiden, The Netherlands)
  Final test concentrations (N=8) for compounds of the invention:
10, 1, 0.3, 0.1, 0.03, 0.01, 0.003, 0.001 µM.

Compound Handling

Stock solutions of compounds (10 mM in 100% DMSO) were provided frozen on dry ice and stored at −20° C. prior to use. From the stock solution, mother solutions were made at a concentration of 500 µM by 20-fold dilution in 26% DMSO. Assay plates were then prepared by appropriate dilution in DMEM medium containing 0.1% BSA. Under these conditions, the maximal final DMSO concentration in the assay was <0.6%.

Cell Preparation

AequoScreen® cells were collected from culture plates with $Ca^{2+}$ and $Mg^{2+}$-free phosphate buffered saline (PBS) supplemented with 5 mM EDTA, pelleted for 2 min at 1000× g, re-suspended in DMEM—Ham's F12 containing 0.1% BSA at a density of $5 \times 10^6$ cells/mL, and incubated overnight at rt in the presence of 5 µM coelenterazine. After loading, cells were diluted with assay buffer to a concentration of $5 \times 10^5$ cells/mL.

Assay Protocol

For agonist testing, 50 µl of the cell suspension was mixed with 50 µl of the appropriate concentration of test compound or ghrelin (reference agonist) in 96-well plates (duplicate samples). Ghrelin (reference agonist) was tested at several concentrations concurrently with the test compounds in order to validate the experiment. The emission of light resulting from receptor activation in response to ghrelin or test compounds was recorded using the Hamamatsu® FDSS 6000 reader (Hamamatsu® Photonics K.K., Japan).

Analysis and Expression of Results

Results were expressed as Relative Light Units (RLU). Concentration response curves were analyzed using GraphPad Prism® (GraphPad Software, Inc., San Diego, Calif.) by non-linear regression analysis (sigmoidal dose-response) based on the equation $E=E_{max}/(1+EC_{50}/C)n$ where E was the measured RLU value at a given agonist concentration (C), $E_{max}$ was the maximal response, $EC_{50}$ was the concentration producing 50% stimulation and n was the slope index. For agonist testing, results for each concentration of test compound are expressed as percent activation relative to the signal induced by ghrelin at a concentration equal to the $EC_{80}$ (i.e. 3.7 nM). $EC_{50}$, Hill slope and % $E_{max}$ values are reported.

TABLE 3

Biological Activity of Representative Compounds of the Invention

| Compound | Binding Activity [$K_i$ (nM)][1] | Receptor[2] |
| --- | --- | --- |
| 101 | A | motilin (human) |
| 102 | B | motilin (human) |
| 103 | C | motilin (human) |
| 104 | C | motilin (human) |
| 105 | C | motilin (human) |
| 106 | C | motilin (human) |
| 107 | C | motilin (human) |
| 108 | C | motilin (human) |
| 109 | B | motilin (human) |
| 110 | C | motilin (human) |
| 111 | B | motilin (human) |
| 112 | B | motilin (human) |
| 113 | B | motilin (human) |
| 114 | B | motilin (human) |
| 115 | C | motilin (human) |
| 116 | B | motilin (human) |
| 118 | B | motilin (human) |
| 119 | B | motilin (human) |
| 124 | C | ghrelin (human) |
| 127 | C | ghrelin (human) |
| 128 | B | ghrelin (human) |
| 131 | B | ghrelin (human) |
| 136 | C | ghrelin (human) |
| 138 | B | ghrelin (human) |
| 139 | B | ghrelin (human) |
| 140 | B | ghrelin (human) |
| 141 | C | ghrelin (human) |
| 143 | C | ghrelin (human) |
| 149 | B | ghrelin (human) |
| 158 | C | ghrelin (human) |
| 160 | B | ghrelin (human) |
| 163 | C | ghrelin (human) |
| 165 | A | ghrelin (human) |
| 166 | C | ghrelin (human) |
| 167 | B | ghrelin (human) |
| 169 | C | ghrelin (human) |

[1]Activity presented indicated in the following ranges: A = 0.01-0.10 µM, B = 0.1-1.0 µM, C = 1.0-10.0 µM
[2]Binding conducted using Standard Methods described in the Examples Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

---

---

What is claimed is:

1. A compound of formula (I):

(I)

wherein $A_4$ is not present, $A_3$ is covalently bonded to T, and X, $A_1$, $A_2$, $A_3$ and T are selected from the group consisting of

| X | $A_1$ |
|---|---|
| NH |  |
| NH |  |
| NH |  |

US 7,550,431 B2
| 61 | | 62 | |
|---|---|---|---|
| -continued | | -continued | |
| NH | 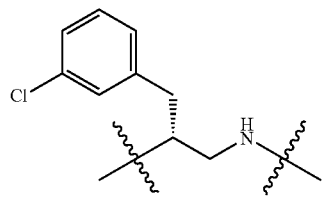 | NH | 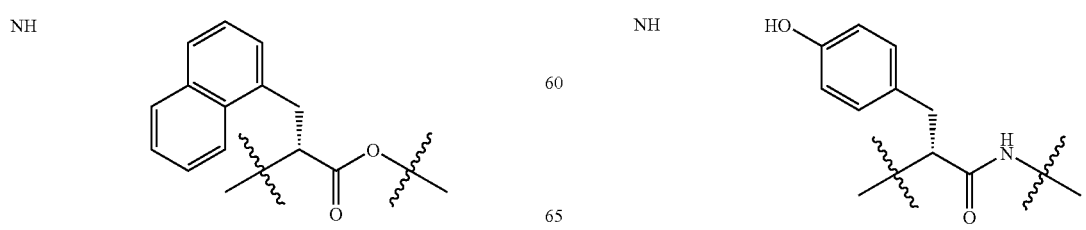 |
| NH | 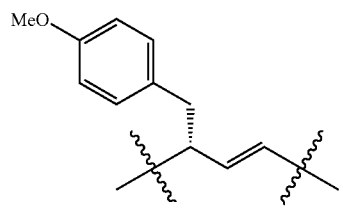 | NH | 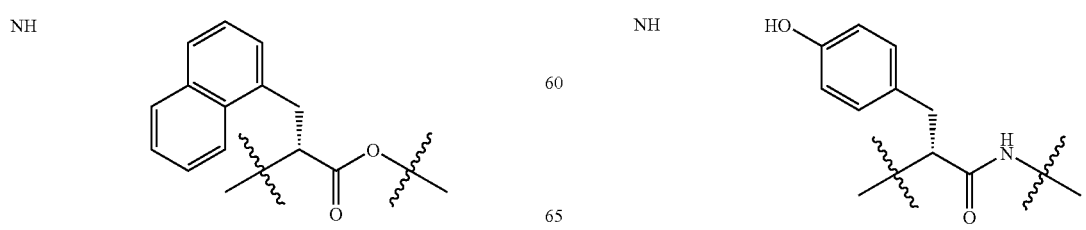 |
| NH | 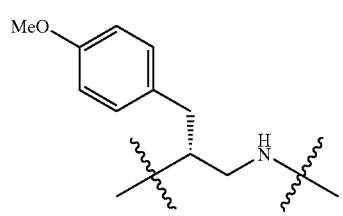 | NH | 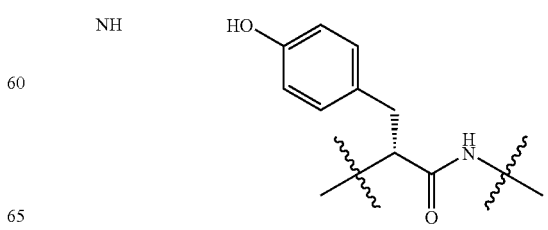 |
| NH | 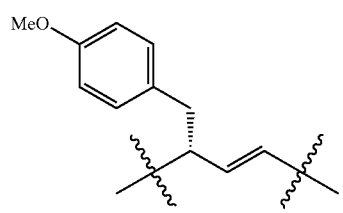 | NH | 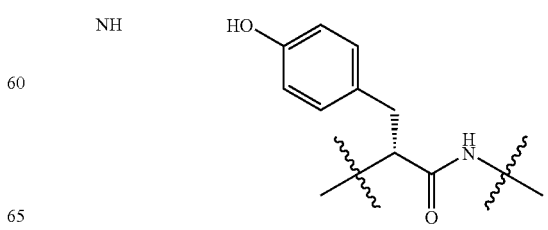 |
| NH | 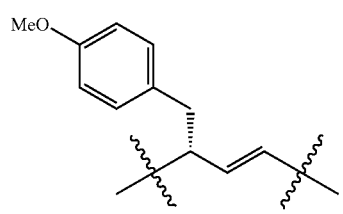 | NH | 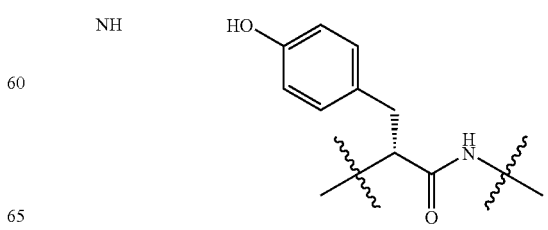 |
| NH | 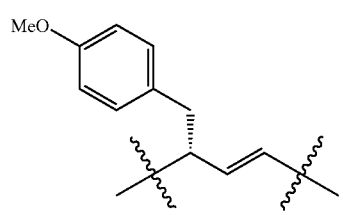 | NH | 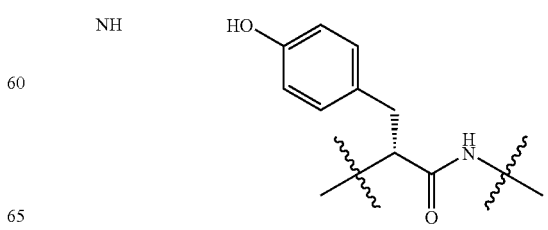 |
| NH | 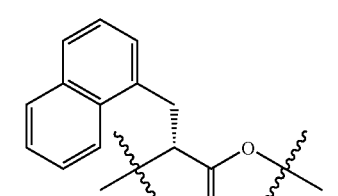 | NH | 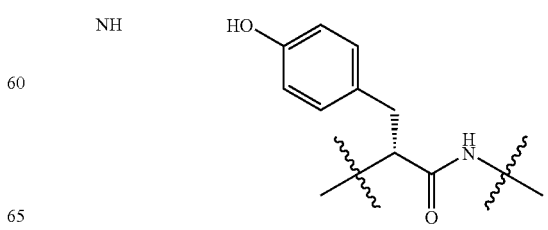 |

-continued
| | |
|---|---|
| NH | 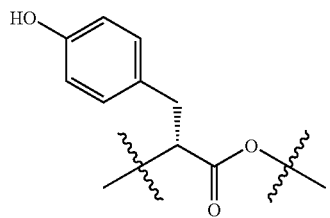 |
| NH | 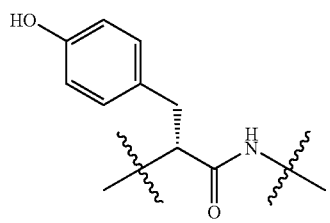 |
| NH | 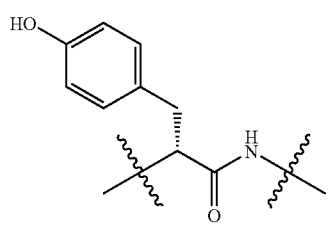 |
| NH | 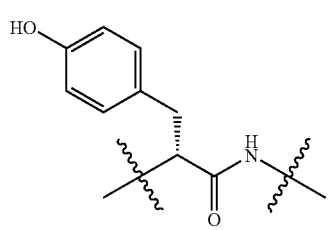 |
| NH | 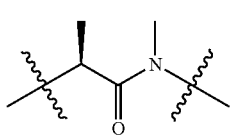 |
| NH | 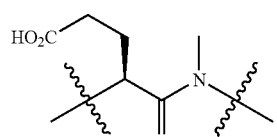 |
| NH | 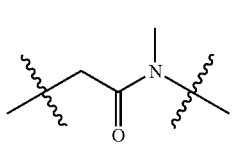 |
| NH | 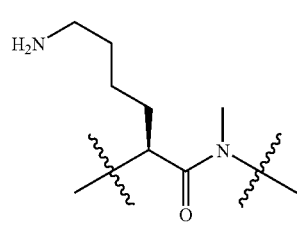 |
-continued
| | |
|---|---|
| NH | 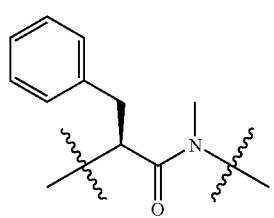 |
| NH | 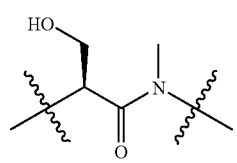 |
| NH | 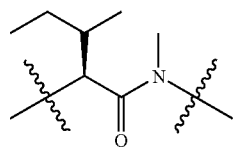 |
| NH | 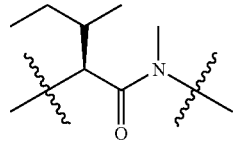 |
| NH | 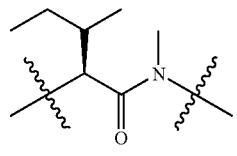 |
| NH | 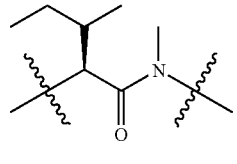 |
| NH | 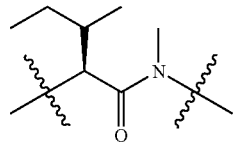 |
| NH | 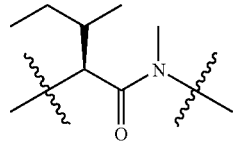 |

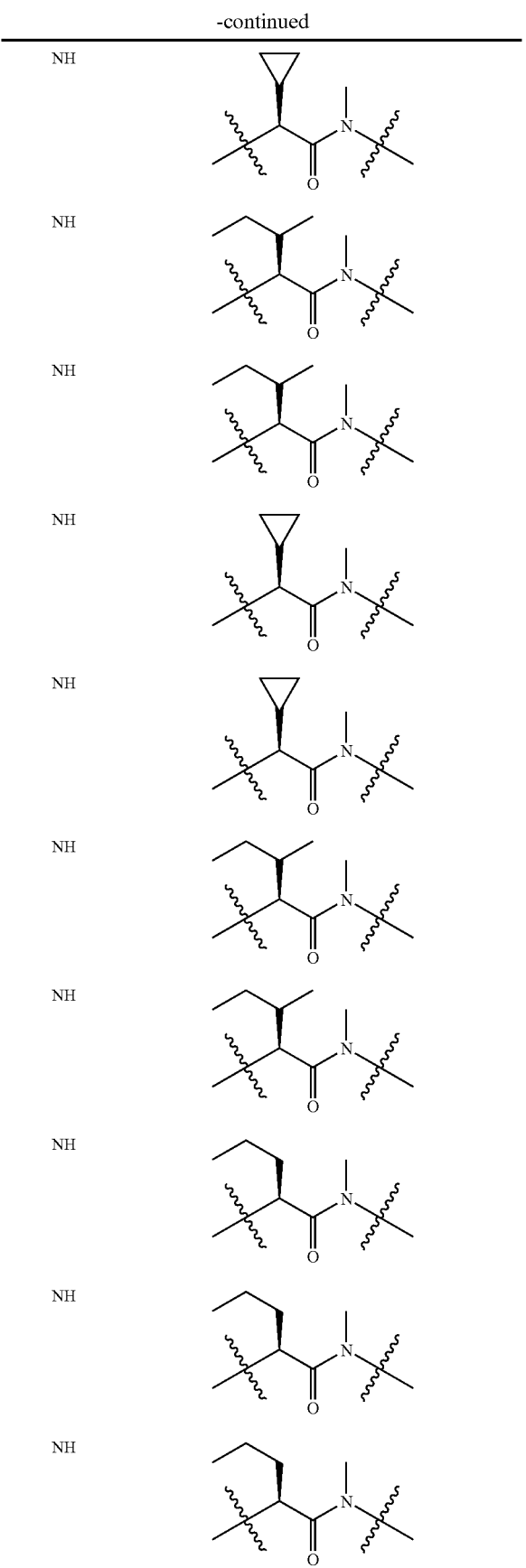
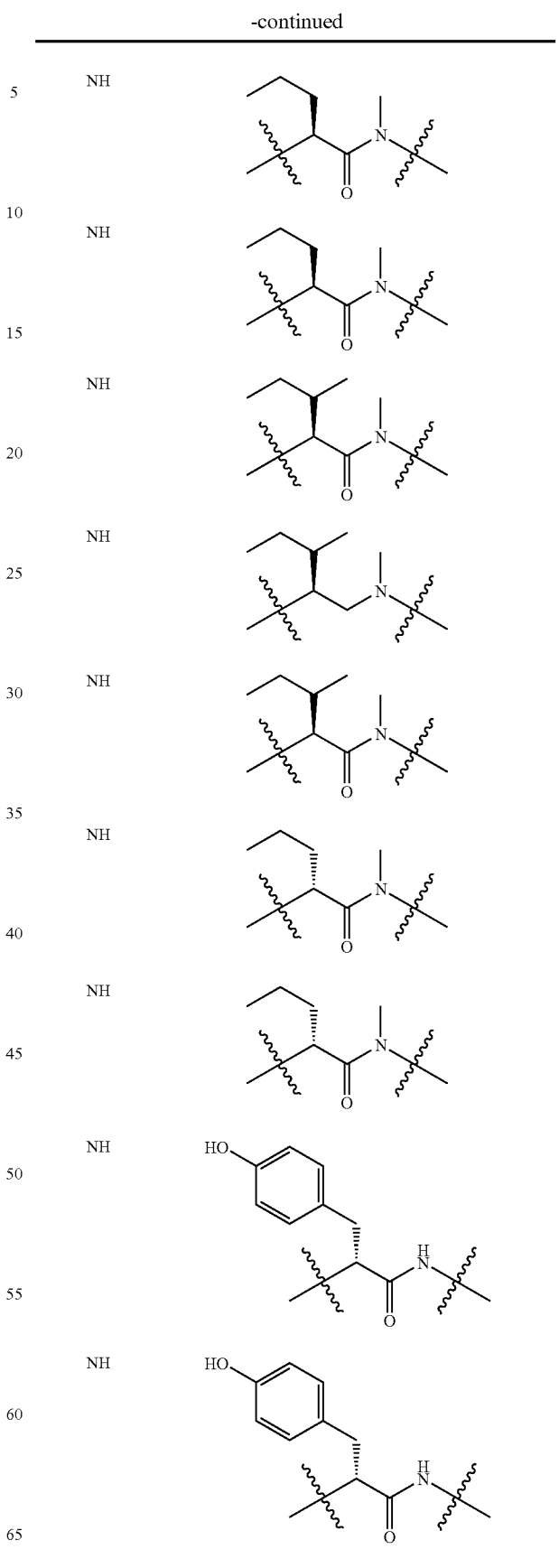

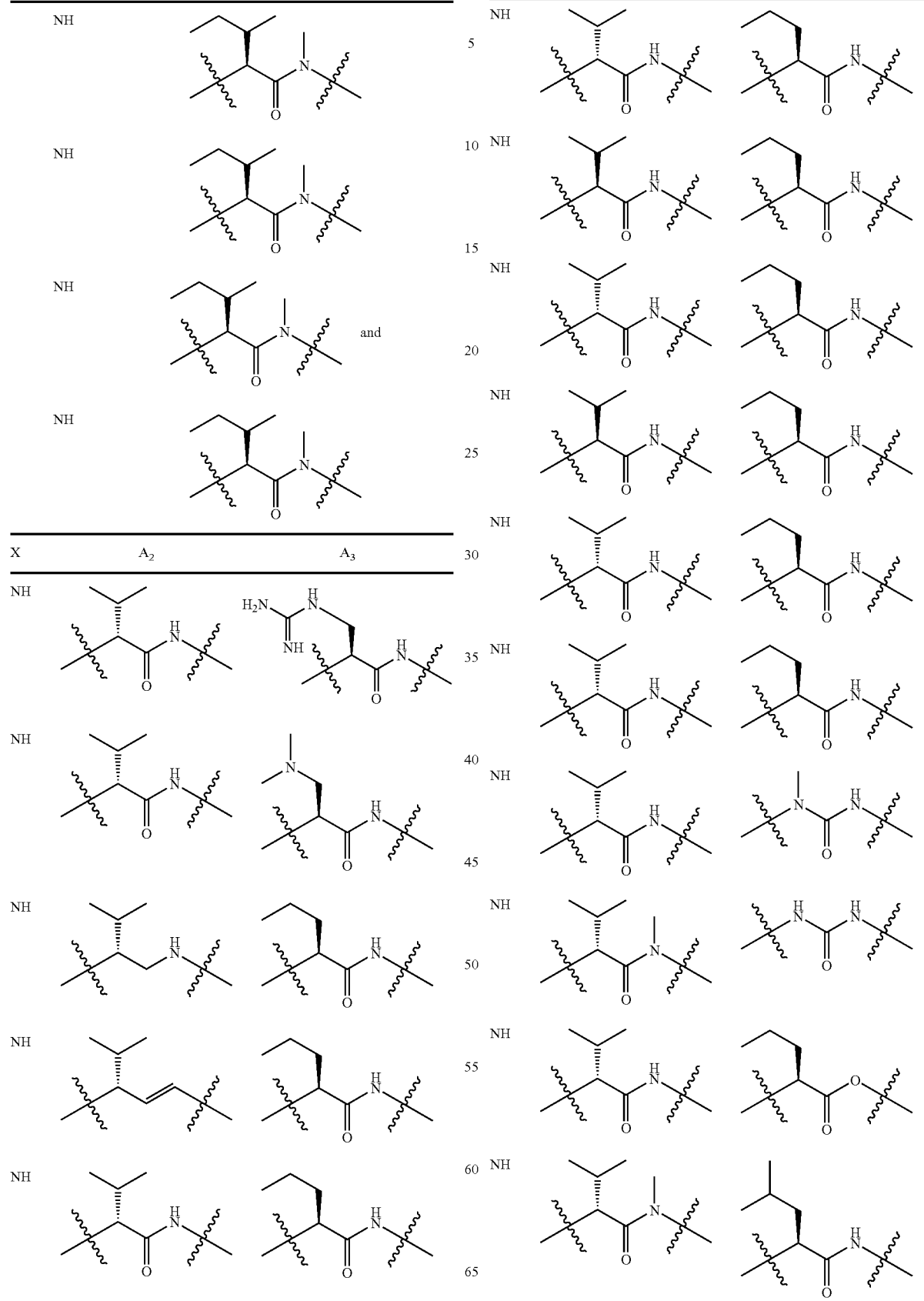

-continued
NH 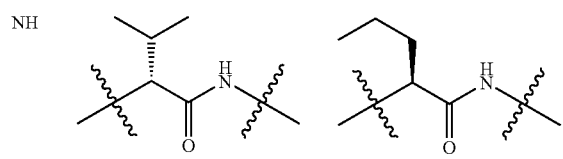
NH 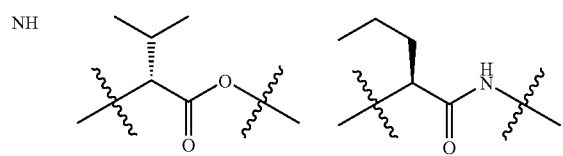
NH 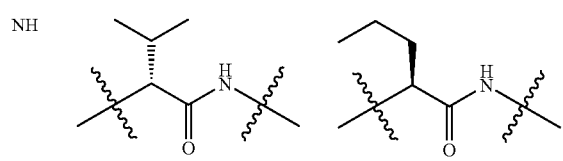
NH 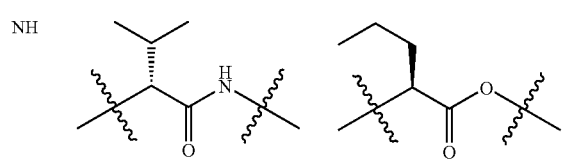
NH 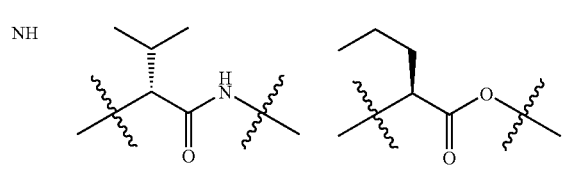
NH 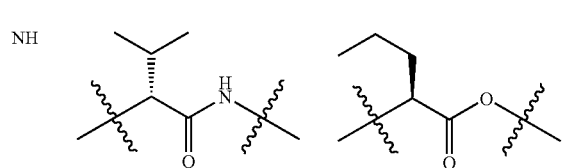
NH 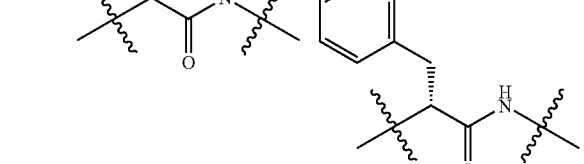
NH 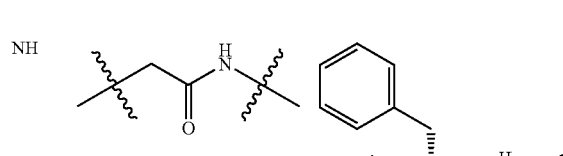
-continued
NH 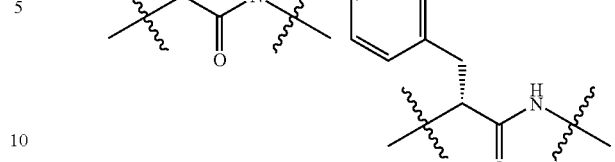
NH 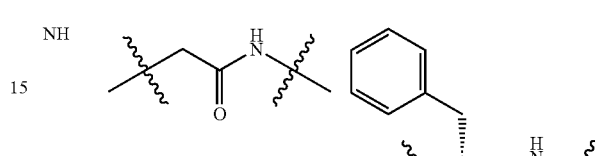
NH 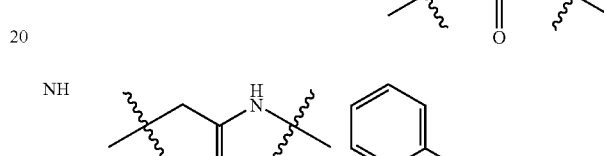
NH 
NH 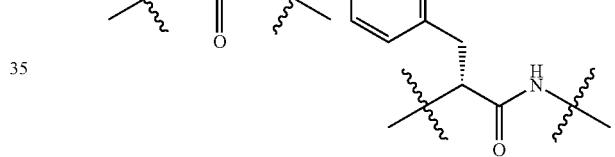
NH 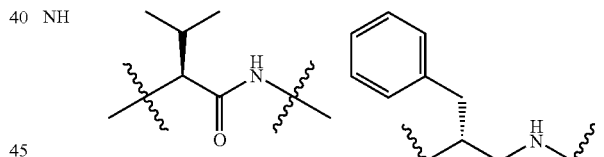
NH 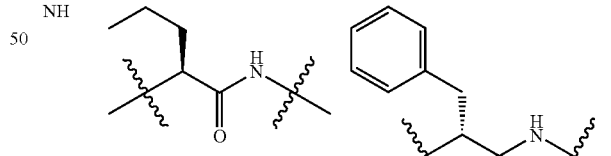
NH 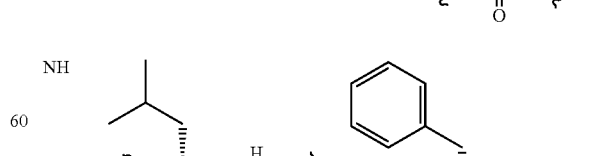

-continued
| | |
|---|---|
| NH 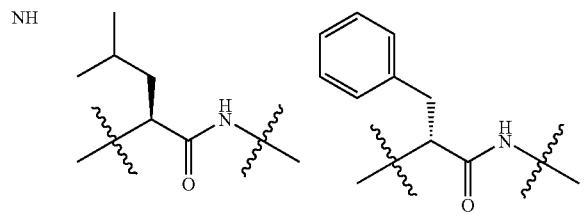 | 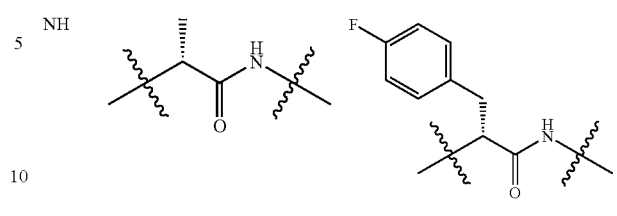 |
| NH 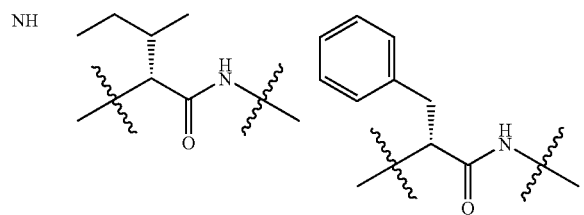 | 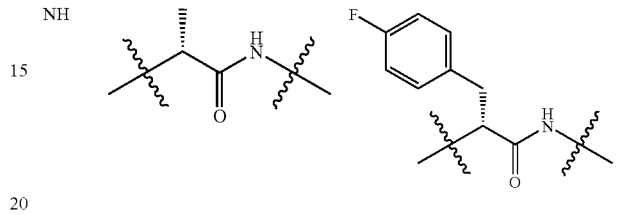 |
| NH 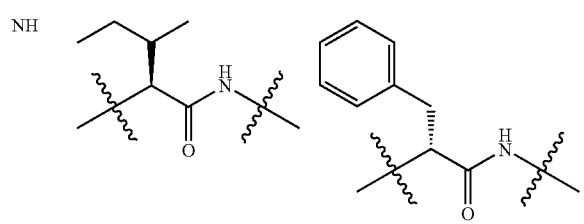 | 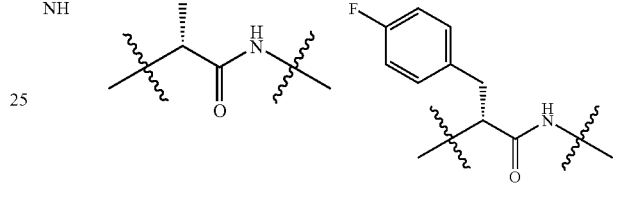 |
| NH 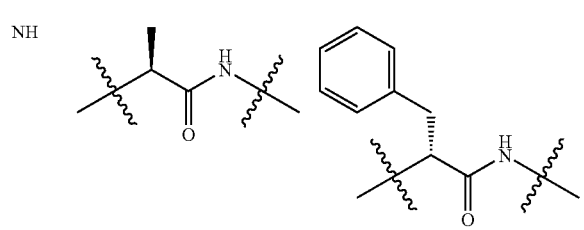 | 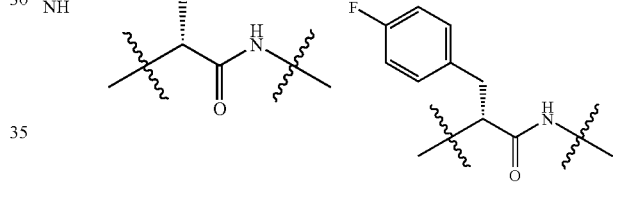 |
| NH 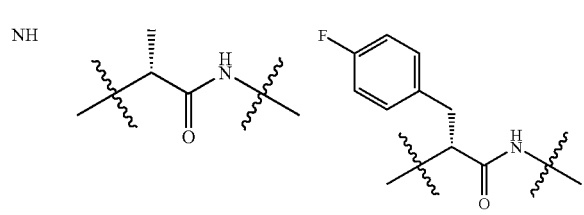 | NH 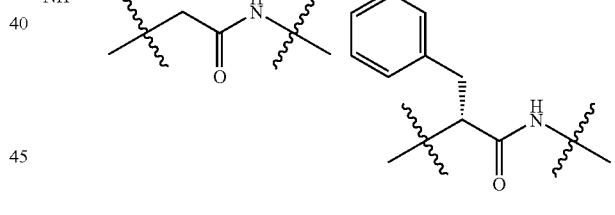 |
| NH 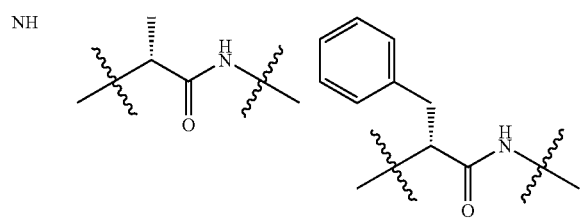 | NH 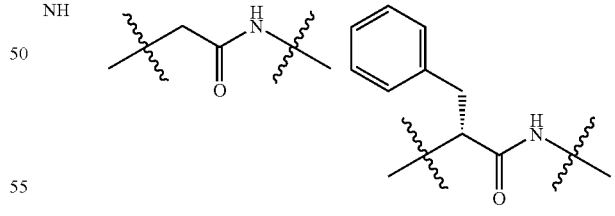 |
| NH 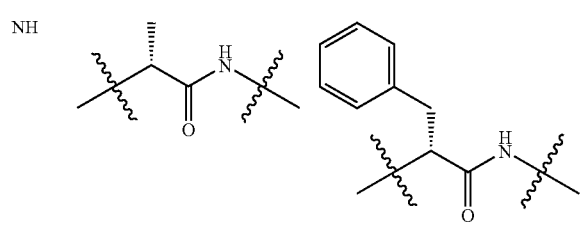 | NH 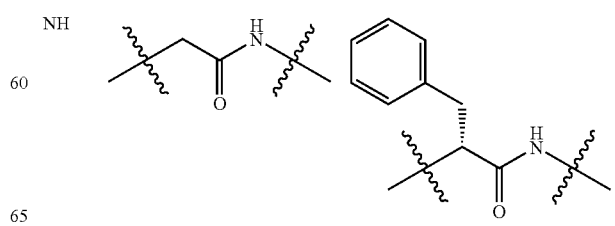 |

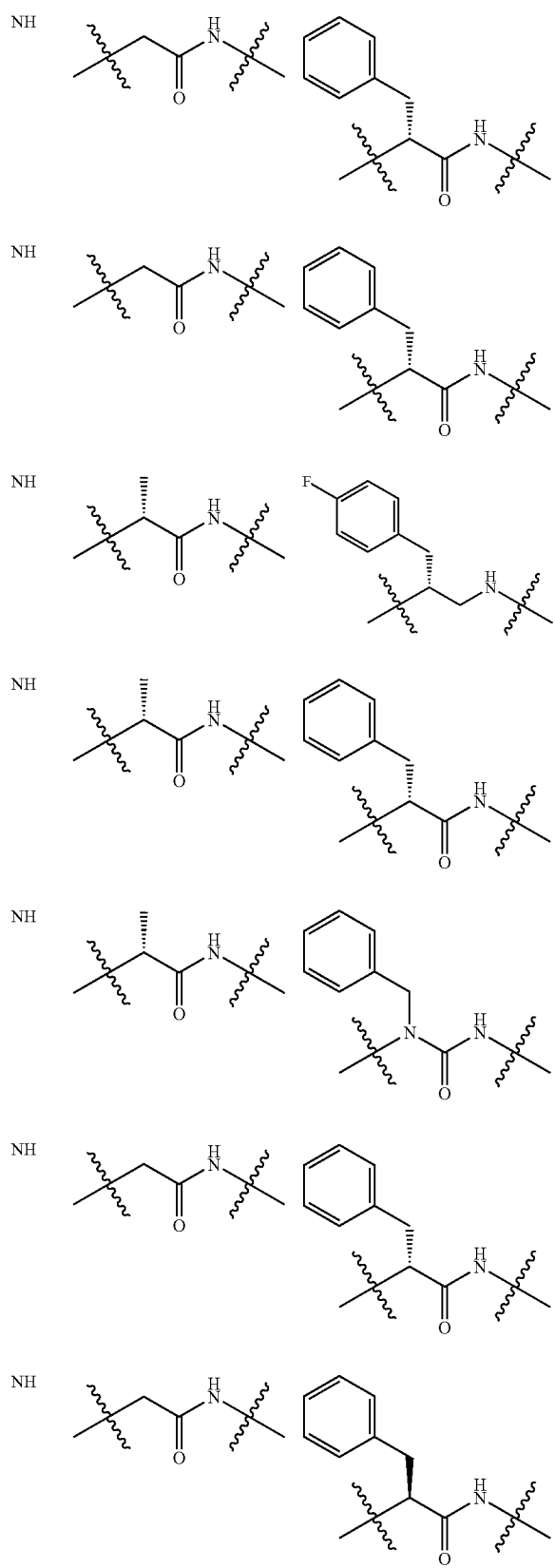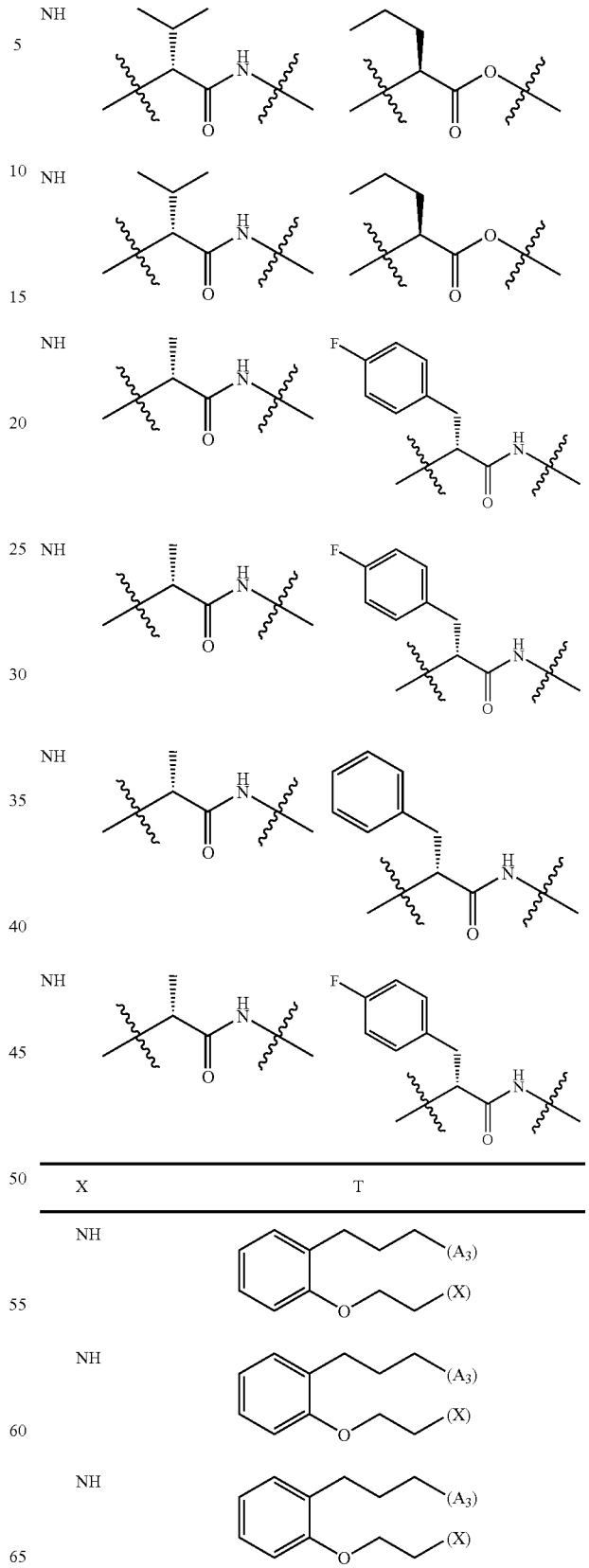
| X | T |
|---|---|
| NH | benzene ring with -(CH2)3-(A3) and -O-CH2CH2-(X) |
| NH | benzene ring with -(CH2)3-(A3) and -O-CH2CH2-(X) |
| NH | benzene ring with -(CH2)3-(A3) and -O-CH2CH2-(X) |

| | | | | |
|---|---|---|---|---|
| NH | 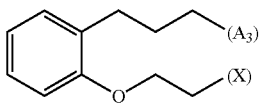 | 5 | NH | 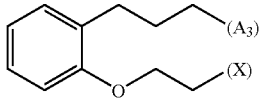 |
| NH | 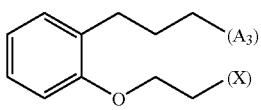 | 10 | NH | 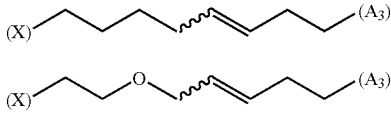 |
| | | | NH | 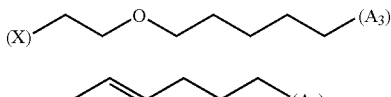 |
| NH | 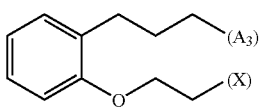 | 15 | NH | 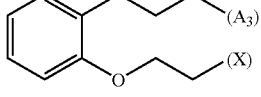 |
| NH | 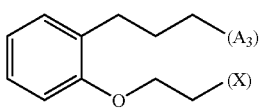 | 20 | NH | 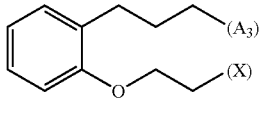 |
| NH | 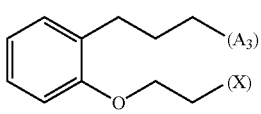 | 25 | NH | 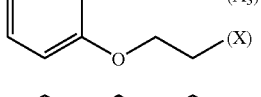 |
| NH | 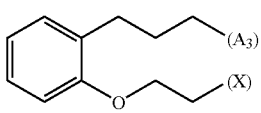 | 30 | NH | 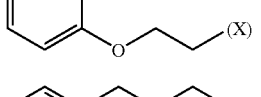 |
| NH | 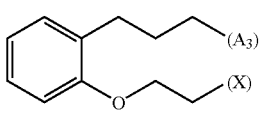 | 35 | NH | 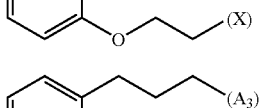 |
| NH | 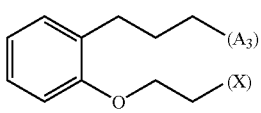 | 40 | NH | 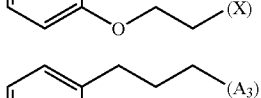 |
| NH | 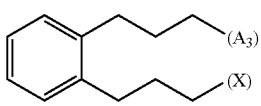 | 45 | NH | 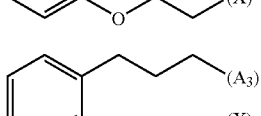 |
| NH | 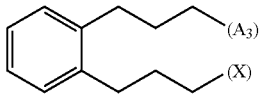 | 50 | NH | 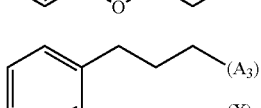 |
| NH | 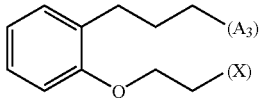 | 55 | NH | 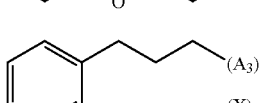 |
| NH | 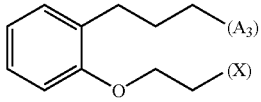 | 60 | NH | 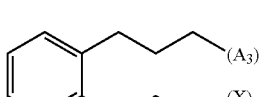 |
| NH | 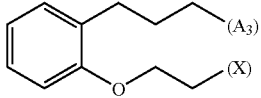 | 65 | | |

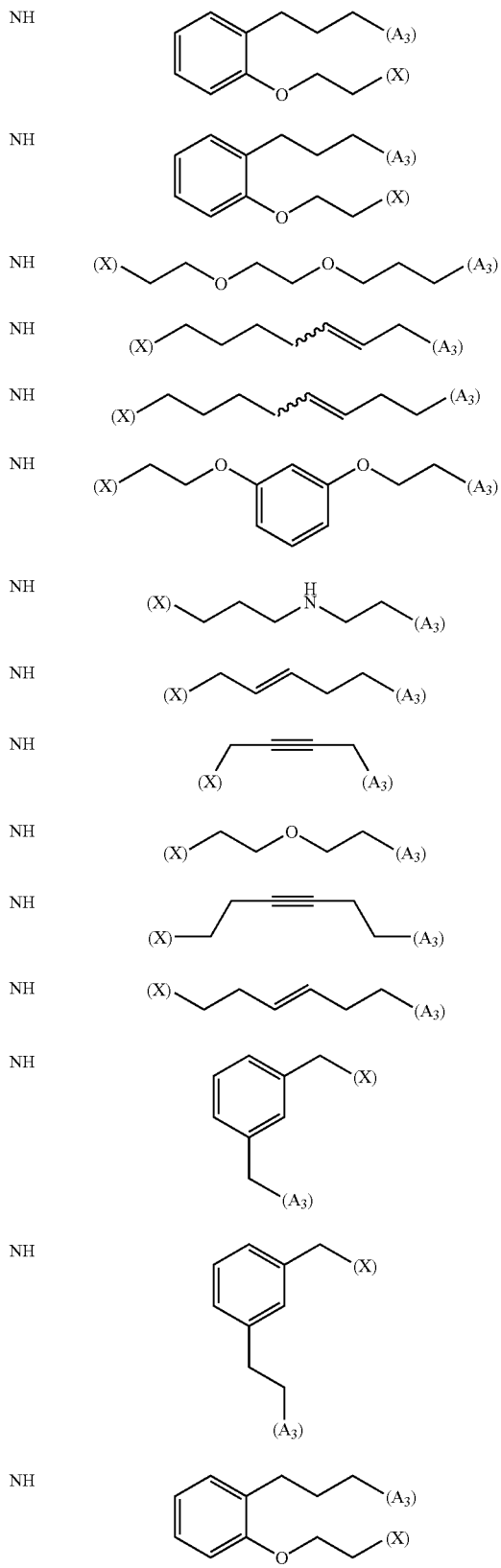
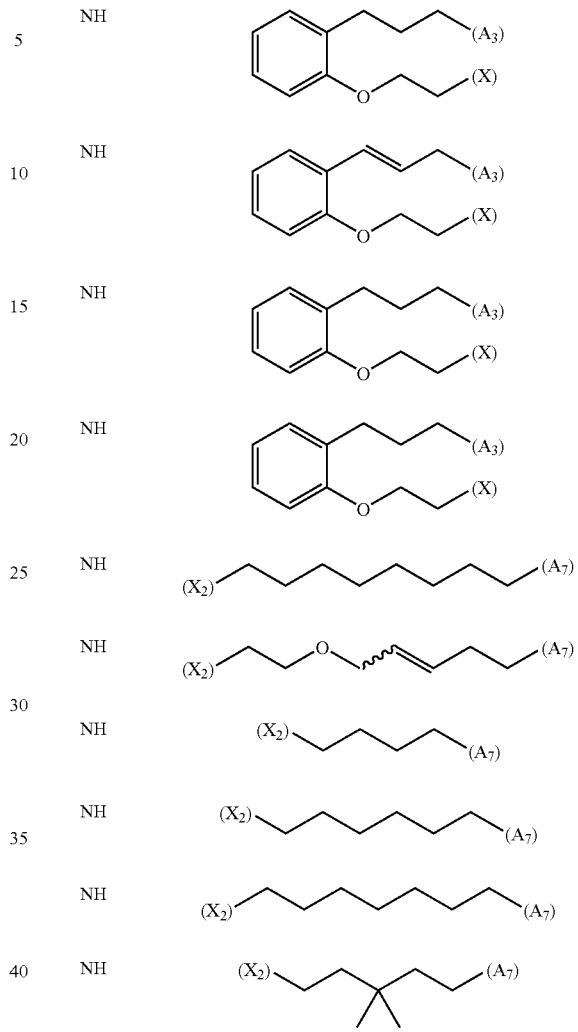
wherein (X) indicates the point of attachment of T to X and (A₃) indicates the point of attachment of T to A₃.
2. An antagonist of a mammalian motilin receptor having the following structure:

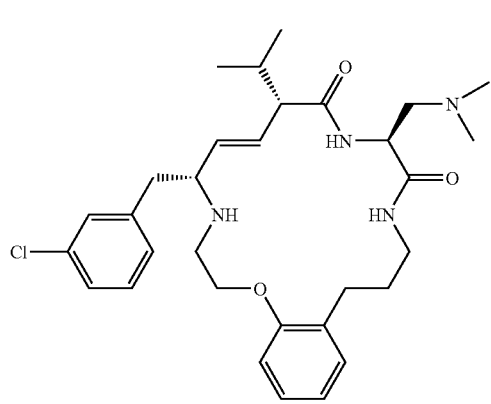
102
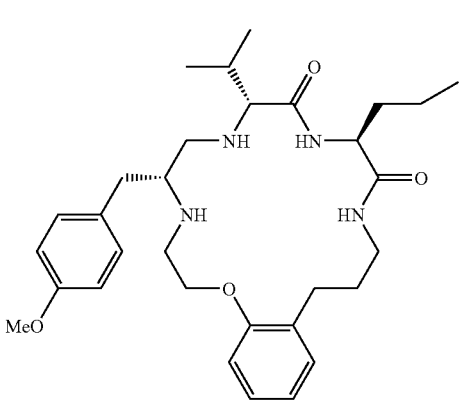
106
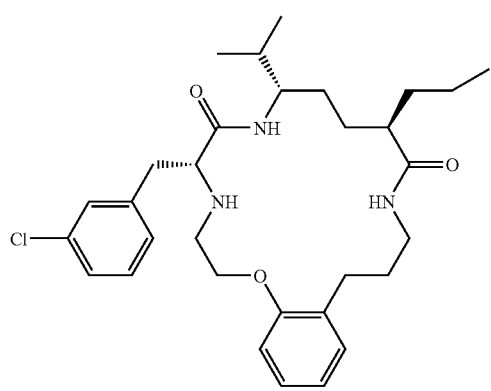
103
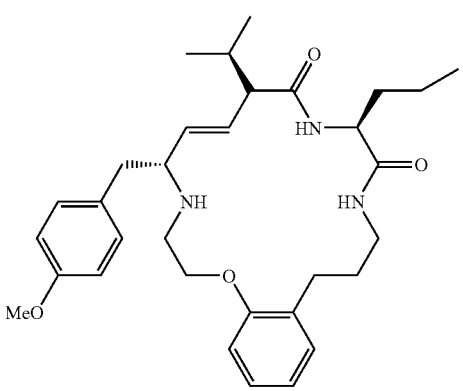
108
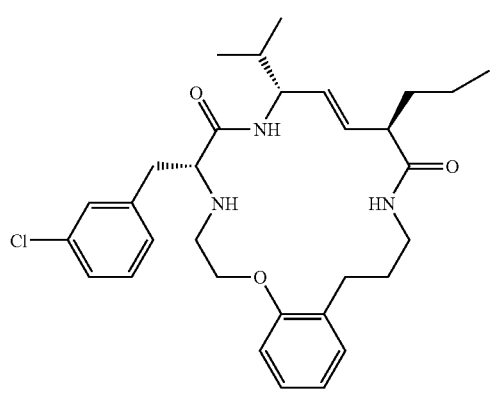
104
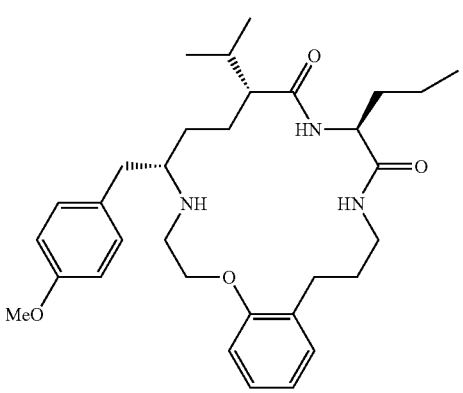
109
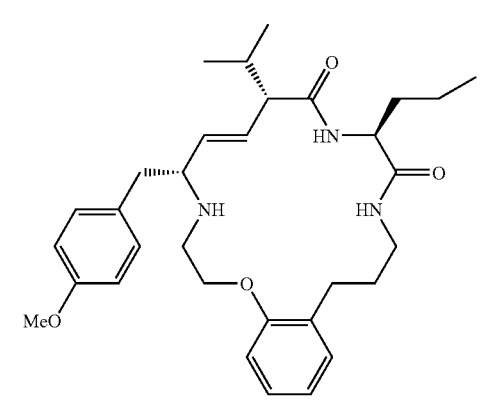
105
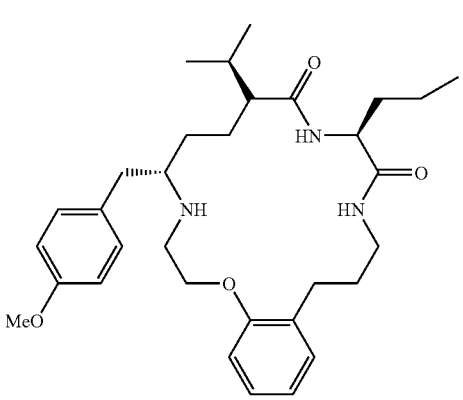
110

-continued
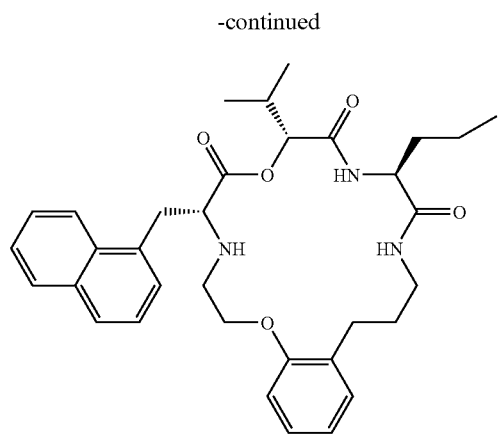
111
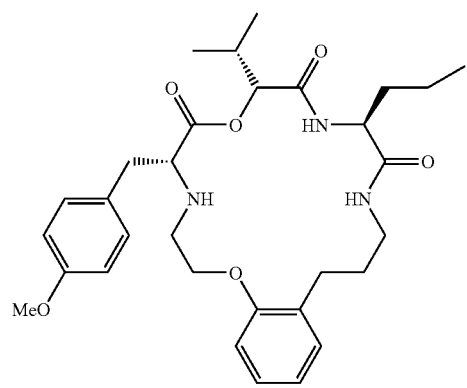
112
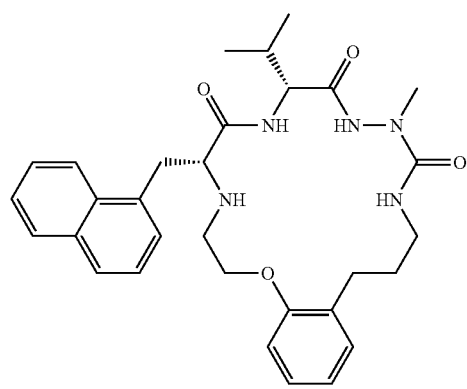
113
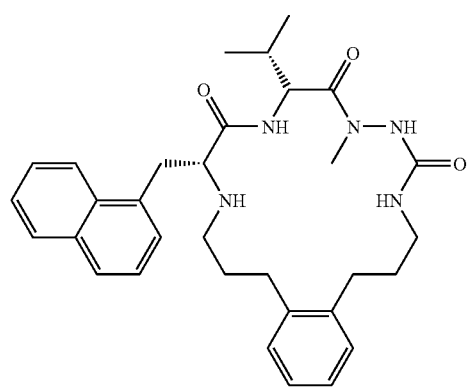
114
-continued
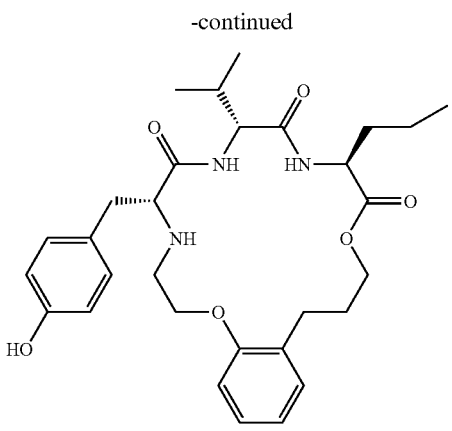
115
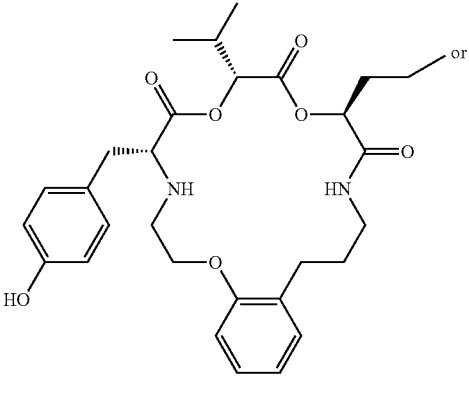
118
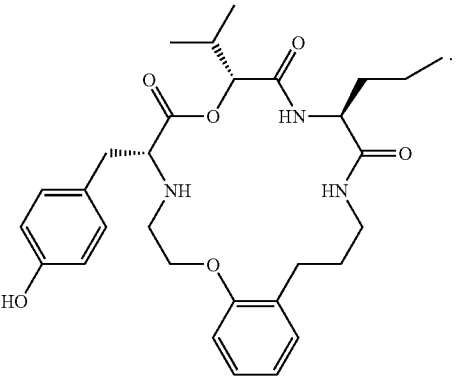
119
3. An agonist of a mammalian ghrelin receptor having the following structure:
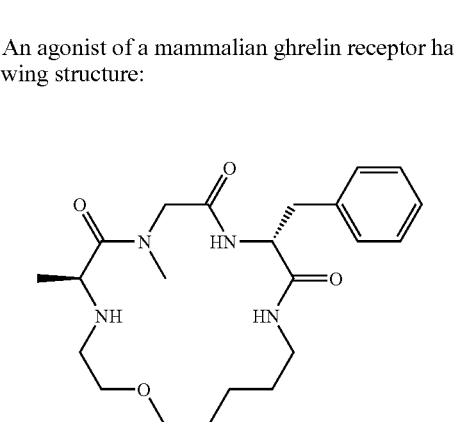
124

-continued

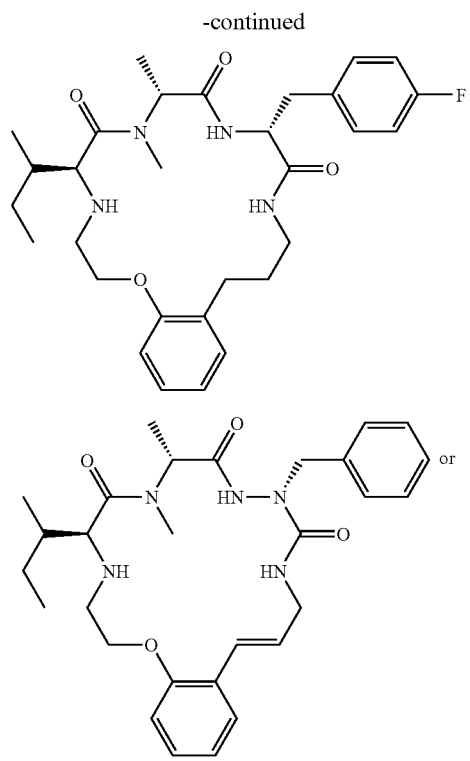
163
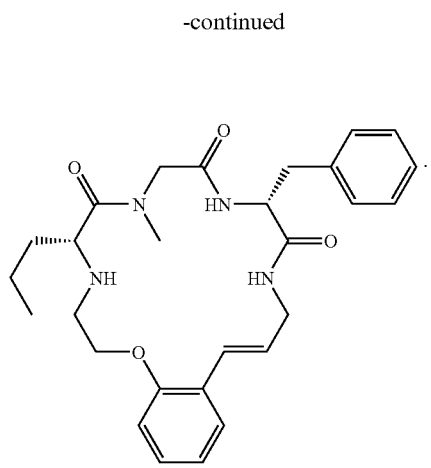
169
165
or
* * * * *

SEQUENCE LISTING

<160> NUMBER OF SEQ ID NOS: 2

<210> SEQ ID NO 1
<211> LENGTH: 22
<212> TYPE: PRT
<213> ORGANISM: Homo sapiens

<400> SEQUENCE: 1

Phe Val Pro Ile Phe Thr Tyr Gly Glu Leu Gln Arg Met Gln Glu Lys
1               5                   10                  15

Glu Arg Asn Lys Gly Gln
            20

<210> SEQ ID NO 2
<211> LENGTH: 28
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: n-octanoyl modification site

<400> SEQUENCE: 2

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25